US009289378B2

(12) United States Patent
Karandikar et al.

(10) Patent No.: US 9,289,378 B2
(45) Date of Patent: Mar. 22, 2016

(54) ANTIMICROBIAL AMORPHOUS COMPOSITIONS

(75) Inventors: Bhalchandra M. Karandikar, Tigard, OR (US); Bruce L. Gibbins, Lake Oswego, OR (US)

(73) Assignee: Avent, Inc., Alpharetta, GA (US)

( * ) Notice: Subject to any disclaimer, the term of this patent is extended or adjusted under 35 U.S.C. 154(b) by 1407 days.

(21) Appl. No.: 11/663,236

(22) PCT Filed: Sep. 19, 2005

(86) PCT No.: PCT/US2005/033600
§ 371 (c)(1),
(2), (4) Date: Mar. 19, 2007

(87) PCT Pub. No.: WO2006/034249
PCT Pub. Date: Mar. 30, 2006

(65) Prior Publication Data
US 2007/0254044 A1    Nov. 1, 2007

Related U.S. Application Data

(60) Provisional application No. 60/611,486, filed on Sep. 20, 2004.

(51) Int. Cl.
| A61K 9/107 | (2006.01) |
| A61K 31/28 | (2006.01) |
| A61K 33/38 | (2006.01) |
| A61K 47/06 | (2006.01) |
| A61K 47/10 | (2006.01) |
| A61K 47/26 | (2006.01) |
| A61K 47/38 | (2006.01) |
| A61P 17/02 | (2006.01) |
| A61P 31/00 | (2006.01) |
| A61K 9/00 | (2006.01) |
| A61K 45/06 | (2006.01) |

(52) U.S. Cl.
CPC ............... *A61K 9/0014* (2013.01); *A61K 9/006* (2013.01); *A61K 9/0063* (2013.01); *A61K 31/28* (2013.01); *A61K 33/38* (2013.01); *A61K 45/06* (2013.01); *A61K 47/06* (2013.01); *A61K 47/10* (2013.01); *A61K 47/26* (2013.01); *A61K 47/38* (2013.01); *A61K 9/107* (2013.01)

(58) Field of Classification Search
None
See application file for complete search history.

(56) References Cited

U.S. PATENT DOCUMENTS

| 2,396,515 | A | * | 3/1946 | Werner et al. ................. 424/618 |
| 2,934,066 | A | | 4/1960 | Stowasser |
| 3,092,552 | A | | 6/1963 | Romans |
| 3,152,094 | A | | 10/1964 | Erner et al. |
| 3,152,904 | A | | 10/1964 | Sorensen et al. |
| 3,157,524 | A | | 11/1964 | Artandi |
| 3,485,658 | A | | 12/1969 | Iler |
| 3,511,764 | A | | 5/1970 | Marans et al. |
| 3,624,835 | A | | 11/1971 | Wyatt |
| 3,645,835 | A | | 2/1972 | Hodgson |
| 3,647,439 | A | | 3/1972 | Bass |
| 3,846,236 | A | | 11/1974 | Updike et al. |
| 3,933,507 | A | | 1/1976 | Von Konig et al. |
| 3,969,498 | A | | 7/1976 | Catania et al. |
| 3,996,141 | A | | 12/1976 | Updike |
| 4,113,658 | A | | 9/1978 | Geus |
| 4,130,517 | A | | 12/1978 | Lundberg et al. |
| 4,136,177 | A | | 1/1979 | Lin et al. |
| 4,136,178 | A | | 1/1979 | Lin et al. |
| 4,260,677 | A | | 4/1981 | Winslow et al. |
| 4,306,551 | A | | 12/1981 | Hymes et al. |
| 4,310,509 | A | | 1/1982 | Berglund et al. |
| 4,320,201 | A | | 3/1982 | Berg et al. |
| 4,328,799 | A | | 5/1982 | LoPiano |
| 4,340,043 | A | | 7/1982 | Seymour |
| 4,364,929 | A | | 12/1982 | Sasmor et al. |
| 4,393,048 | A | | 7/1983 | Mason, Jr. et al. |
| 4,474,571 | A | | 10/1984 | Lasley |
| 4,483,688 | A | | 11/1984 | Akiyama |
| 4,529,623 | A | | 7/1985 | Maggs |
| 4,604,384 | A | | 8/1986 | Smith et al. |
| 4,608,041 | A | | 8/1986 | Nielsen |
| 4,612,337 | A | | 9/1986 | Fox, Jr. et al. |
| 4,624,656 | A | | 11/1986 | Clark et al. |

(Continued)

FOREIGN PATENT DOCUMENTS

| DE | 19631421 A1 | 2/1998 |
| EP | 0072251 | 2/1983 |

(Continued)

OTHER PUBLICATIONS

Milk Composition & Synthesis Resourse Library, Milk Composition-Minerals [retrieved on Dec. 5, 2010], retrieved from the internet<URL:http://classes.ansci.illinois.edu/ansc438/milkcompsynth/milkcomp_minerals.html>.*

(Continued)

*Primary Examiner* — Abigail Fisher
*Assistant Examiner* — Frank Choi
(74) *Attorney, Agent, or Firm* — Dority & Manning, P.A.

(57) ABSTRACT

The present invention comprises compositions and methods for providing antimicrobial compositions. The antimicrobial compositions comprise gel delivery vehicles comprising stabilized silver, wherein ionic silver is provided to a site for antimicrobial purposes. Methods of making and using such compositions are taught, including application of the silver-containing gel compositions to wounds, burns, abrasions, cuts, surgical incision, sites where skin or organ integrity has been breached, and other sites to supply an antimicrobial environment.

18 Claims, No Drawings

(56) References Cited

U.S. PATENT DOCUMENTS

| | | |
|---|---|---|
| 4,686,211 A | 8/1987 | Hara et al. |
| 4,708,821 A | 11/1987 | Shimokawa et al. |
| 4,721,724 A | 1/1988 | Stettendorf et al. |
| 4,747,847 A | 5/1988 | Magruder et al. |
| 4,782,819 A | 11/1988 | Adair |
| 4,801,291 A | 1/1989 | Loori |
| 4,902,503 A | 2/1990 | Umemura et al. |
| 4,915,694 A | 4/1990 | Yamamoto et al. |
| 4,969,881 A | 11/1990 | Viesturs |
| 5,023,082 A | 6/1991 | Friedman et al. |
| 5,049,139 A | 9/1991 | Gilchrist |
| 5,076,265 A | 12/1991 | Wokalek |
| 5,086,620 A | 2/1992 | Spears |
| 5,091,171 A | 2/1992 | Yu et al. |
| 5,100,668 A | 3/1992 | Edelman et al. |
| 5,128,326 A | 7/1992 | Balazs et al. |
| 5,149,524 A | 9/1992 | Sherba et al. |
| 5,151,271 A | 9/1992 | Otsuka et al. |
| 5,158,772 A | 10/1992 | Davis |
| 5,175,229 A | 12/1992 | Braatz et al. |
| 5,181,914 A | 1/1993 | Zook |
| 5,196,190 A | 3/1993 | Nangia et al. |
| 5,236,421 A | 8/1993 | Becher |
| 5,270,358 A | 12/1993 | Asmus |
| 5,326,567 A | 7/1994 | Capelli |
| 5,342,528 A | 8/1994 | Adachi et al. |
| 5,354,862 A | 10/1994 | Hsu |
| 5,407,685 A | 4/1995 | Malchesky et al. |
| 5,429,591 A | 7/1995 | Yamamoto et al. |
| 5,432,077 A | 7/1995 | Farrah |
| 5,447,492 A | 9/1995 | Cartmell et al. |
| 5,453,401 A | 9/1995 | Grivna et al. |
| 5,454,886 A | 10/1995 | Burrell et al. |
| 5,464,610 A | 11/1995 | Hayes, Jr. et al. |
| 5,470,585 A | 11/1995 | Gilchrist |
| 5,503,840 A | 4/1996 | Jacobson et al. |
| 5,508,038 A | 4/1996 | Wang et al. |
| 5,508,417 A | 4/1996 | Osei-Gyimah et al. |
| 5,516,502 A | 5/1996 | Dickerson |
| 5,527,534 A | 6/1996 | Myhling |
| 5,567,495 A | 10/1996 | Modak et al. |
| 5,569,207 A | 10/1996 | Gisselberg et al. |
| 5,593,683 A | 1/1997 | Viegas et al. |
| 5,599,296 A | 2/1997 | Spears |
| 5,603,946 A | 2/1997 | Constantine |
| 5,614,568 A | 3/1997 | Mawatari et al. |
| 5,660,854 A | 8/1997 | Haynes et al. |
| 5,681,579 A | 10/1997 | Freeman |
| 5,683,713 A | 11/1997 | Blank et al. |
| 5,693,624 A | 12/1997 | Hardy et al. |
| 5,695,777 A | 12/1997 | Donovan et al. |
| 5,709,870 A | 1/1998 | Yoshimura et al. |
| 5,725,491 A | 3/1998 | Tipton et al. |
| 5,735,251 A | 4/1998 | Hyodo et al. |
| 5,736,582 A | 4/1998 | Devillez |
| 5,744,151 A | 4/1998 | Capelli |
| 5,753,251 A | 5/1998 | Burrell et al. |
| 5,792,090 A | 8/1998 | Ladin |
| 5,804,213 A | 9/1998 | Rolf |
| 5,820,918 A | 10/1998 | Ronan et al. |
| 5,830,496 A | 11/1998 | Freeman |
| 5,833,665 A | 11/1998 | Bootman et al. |
| 5,840,283 A | 11/1998 | Sorenson et al. |
| 5,853,742 A | 12/1998 | Bartolone et al. |
| 5,855,570 A | 1/1999 | Scherson et al. |
| 5,863,548 A | 1/1999 | Elder |
| 5,863,864 A | 1/1999 | Plath et al. |
| 5,869,073 A | 2/1999 | Sawan et al. |
| 5,908,693 A | 6/1999 | Delgado et al. |
| 5,927,317 A | 7/1999 | Hsia |
| 5,928,174 A | 7/1999 | Gibbins |
| 5,951,458 A | 9/1999 | Hastings et al. |
| 5,961,996 A | 10/1999 | Garson et al. |
| 5,965,204 A | 10/1999 | Sodervall et al. |
| 5,972,317 A | 10/1999 | Sorenson et al. |
| 5,993,790 A | 11/1999 | Strauss |
| 6,000,403 A | 12/1999 | Cantwell |
| 6,004,667 A | 12/1999 | Sakurada et al. |
| 6,011,194 A | 1/2000 | Buglino et al. |
| 6,014,585 A | 1/2000 | Stoddard |
| 6,042,845 A | 3/2000 | Sun et al. |
| 6,051,614 A | 4/2000 | Hirai et al. |
| 6,099,805 A | 8/2000 | Hartlove |
| 6,103,868 A | 8/2000 | Heath et al. |
| 6,110,447 A | 8/2000 | Ramin et al. |
| 6,113,287 A | 9/2000 | Merz et al. |
| 6,143,794 A | 11/2000 | Chaudhuri et al. |
| 6,159,977 A | 12/2000 | Reeves |
| 6,187,290 B1 | 2/2001 | Gilchrist et al. |
| 6,191,339 B1 | 2/2001 | Gueret |
| 6,201,164 B1 * | 3/2001 | Wulff et al. .................... 602/48 |
| 6,214,360 B1 | 4/2001 | Richter et al. |
| 6,224,622 B1 | 5/2001 | Kotzev |
| 6,231,840 B1 | 5/2001 | Buck |
| 6,235,964 B1 | 5/2001 | Kadash et al. |
| 6,248,342 B1 | 6/2001 | Trogolo et al. |
| 6,264,927 B1 | 7/2001 | Monahan |
| 6,270,811 B1 | 8/2001 | Fregonese |
| 6,316,084 B1 | 11/2001 | Claus et al. |
| 6,326,524 B1 | 12/2001 | Fattman et al. |
| 6,355,858 B1 | 3/2002 | Gibbins |
| 6,468,989 B1 | 10/2002 | Chang et al. |
| 6,471,982 B1 | 10/2002 | Lydon et al. |
| 6,530,895 B1 | 3/2003 | Keirn |
| 6,605,751 B1 | 8/2003 | Gibbins et al. |
| 6,669,981 B2 | 12/2003 | Parsons et al. |
| 6,716,895 B1 | 4/2004 | Terry |
| 6,897,349 B2 | 5/2005 | Gibbins et al. |
| 6,921,529 B2 | 7/2005 | Maley |
| 7,129,389 B1 | 10/2006 | Watson |
| 7,160,553 B2 | 1/2007 | Gibbins et al. |
| 7,166,330 B2 | 1/2007 | Takahashi et al. |
| 7,189,410 B1 | 3/2007 | Drohan et al. |
| 7,576,255 B2 | 8/2009 | Gibbins et al. |
| 2001/0026810 A1 | 10/2001 | McGhee et al. |
| 2001/0041188 A1 | 11/2001 | Gibbins et al. |
| 2002/0001604 A1 | 1/2002 | Shigeru et al. |
| 2002/0042587 A1 | 4/2002 | Murdock |
| 2002/0073891 A1 | 6/2002 | Parsons et al. |
| 2002/0082340 A1 | 6/2002 | Hanke et al. |
| 2003/0041188 A1 | 2/2003 | Han et al. |
| 2003/0083610 A1 | 5/2003 | McGrath et al. |
| 2003/0093057 A1 | 5/2003 | Zhang et al. |
| 2003/0186955 A1 | 10/2003 | Vange et al. |
| 2004/0010215 A1 | 1/2004 | Gibbins et al. |
| 2004/0062733 A1 | 4/2004 | Birnbaum |
| 2004/0082925 A1 | 4/2004 | Patel |
| 2004/0096410 A1 | 5/2004 | Maley et al. |
| 2004/0108462 A1 | 6/2004 | Besesty et al. |
| 2004/0127025 A1 | 7/2004 | Crocker et al. |
| 2004/0147618 A1 * | 7/2004 | Lee et al. .................... 516/78 |
| 2004/0170545 A1 | 9/2004 | Emanuel |
| 2004/0173056 A1 | 9/2004 | McNally et al. |
| 2004/0180093 A1 | 9/2004 | Burton et al. |
| 2004/0253536 A1 | 12/2004 | Park et al. |
| 2004/0254532 A1 | 12/2004 | Mehier |
| 2005/0008861 A1 | 1/2005 | Yadav et al. |
| 2005/0029121 A1 | 2/2005 | Monzyk et al. |
| 2005/0035327 A1 * | 2/2005 | Canada et al. .......... 252/182.15 |
| 2005/0186135 A1 | 8/2005 | Howes |
| 2005/0265894 A1 | 12/2005 | Monzyk et al. |
| 2006/0276740 A1 | 12/2006 | Bagley |
| 2007/0003603 A1 | 1/2007 | Karandikar et al. |
| 2007/0207335 A1 | 9/2007 | Karandikar et al. |
| 2007/0293800 A1 | 12/2007 | McMaken et al. |
| 2009/0035342 A1 | 2/2009 | Karandikar et al. |
| 2010/0034882 A1 | 2/2010 | Gibbins et al. |

FOREIGN PATENT DOCUMENTS

| | | |
|---|---|---|
| EP | 0297769 A1 | 1/1989 |
| EP | 0489206 | 6/1992 |
| EP | 0500387 | 8/1992 |
| EP | 0707793 | 4/1996 |

(56) References Cited

FOREIGN PATENT DOCUMENTS

| | | | |
|---|---|---|---|
| EP | 0709101 | A2 | 5/1996 |
| EP | 1245239 | A1 | 10/2002 |
| EP | 1388561 | A2 | 2/2004 |
| GB | 863875 | A | 3/1961 |
| GB | 1471013 | | 4/1977 |
| GB | 1554002 | | 10/1979 |
| GB | 2134791 | | 8/1984 |
| GB | 2134791 | A | 8/1984 |
| JP | 05-271718 | A | 10/1993 |
| JP | 06-145060 | A | 5/1994 |
| JP | 6248549 | A | 9/1994 |
| JP | 7097767 | A | 4/1995 |
| JP | 11302119 | A | 11/1999 |
| JP | 2003529630 | A | 10/2003 |
| JP | 2004137615 | A | 5/2004 |
| JP | 2004161632 | A | 6/2004 |
| WO | WO 84/17121 | | 5/1984 |
| WO | WO-88/06894 | A1 | 9/1988 |
| WO | WO-90/03810 | A1 | 4/1990 |
| WO | WO-96/11572 | A1 | 4/1996 |
| WO | WO 98/06260 | | 2/1998 |
| WO | WO-98/06260 | A1 | 2/1998 |
| WO | WO-98/20719 | A1 | 5/1998 |
| WO | WO-99/15101 | A2 | 4/1999 |
| WO | WO 99/25395 | | 5/1999 |
| WO | WO-9926666 | A2 | 6/1999 |
| WO | WO 00/09173 | | 2/2000 |
| WO | WO-00/15202 | A2 | 3/2000 |
| WO | WO-01/11955 | A2 | 2/2001 |
| WO | WO 01/24839 | | 4/2001 |
| WO | WO-01/49258 | A2 | 7/2001 |
| WO | WO 02/26039 | | 4/2002 |
| WO | WO 02/43743 | | 6/2002 |
| WO | WO 02/061403 | | 8/2002 |
| WO | WO-02/076518 | A1 | 10/2002 |
| WO | WO 03/002089 | | 1/2003 |
| WO | WO-03/080231 | A1 | 10/2003 |
| WO | WO 2004/001880 | | 12/2003 |
| WO | WO-2004/010952 | A2 | 2/2004 |
| WO | WO 2004/028255 | | 4/2004 |
| WO | WO-2004/056404 | A2 | 7/2004 |
| WO | WO-2006/015317 | A2 | 2/2006 |
| WO | WO-2006/026026 | A2 | 3/2006 |
| WO | WO-2006/034249 | A2 | 3/2006 |
| WO | WO-2007/095058 | A2 | 8/2007 |
| WO | WO-2007/127236 | A2 | 11/2007 |
| WO | WO-2008/131070 | A1 | 10/2008 |

OTHER PUBLICATIONS

Puchtler et al., Demonstration of Phosphates in Calcium Deposits: A Modification of von Kossa's Reaction, Histochemistry (1978), vol. 56, pp. 177-185.*

International Search Report for related PCT Application No. PCT/US05/033600 dated Apr. 18, 2007.

Schacht, Etienne H., Hydrogel Drug Delivery Systems, Institute of Organic Chemistry, State University, pp. 259-278.

Chase, Ph.D., Grafton D., Pharmaceutical Science by Remington, 14th Edition., Mack Publishing Co., Rheology, Newtonian Flow-Plastic Flow-Pseudoplastic Flow-Dilatant Flow-Methods for Measuring Viscosity-Polymer Solutions-Thixotrophy-Pharmaceutical Applications, pp. 359-371, 1970.

Ratner, Buddy D. et al., ACS Symposium Series, No. 31, The American Chemical Society, Synthetic Hydrogels for Biomedical Applications, pp. 1-36.

Handbook of Common Polymers, Scott & Roff, Jr., W.J., The Chemical Company, Polyvinyl Alcohol Including Insolubilised Fibres, Cleveland, Ohio, pp. 72-197.

Hackh's Chemical Dictionary, 4th Edition, McGraw Hill Book Co., New York, p. 451, 1969.

Fox, Jr., Charles L., Silver Sulfadiazine-A New Topical, Arch. Surg., vol. 96, pp. 184-188, 1968.

Russell, A.D. et al., Antimicrobial Activity and Action of Silver, Progress in Medicinal Chemistry, vol. 31, pp. 351-370, 1994.

Grier Ph.D., N., Silver and Its Compounds, Disinfection, Sterilization and Preservation, 3rd Edition, Seymour S. Block, Lea & Febiger, Chapter 18, pp. 375-389, 1983.

Cooper, Rose, "A Review of the Evidence for the Use of Topical Antimicrobial Agents in Wound Care", World Wide Wounds, Feb. 2004, pp. 1-15.

Silver, Simon, "Bacterial Silver Reistance: Molecular Biology and Uses and Misuses of Silver Compounds", FEMS Microbiology Reviews, Apr. 29, 2003, pp. 341-353.

Price, William R. et al., Silver Nitrate Burn Dressing, Treatment of Seventy Burned Persons, American Journal of Surgery, vol. 112, Nov. 1966, pp. 674-680.

Gibbins, Ph.D., Bruce, "The Antimicrobial Benefits of Silver and the Relevance of Microlattice Technology", OstomyWound Management, Feb. 2003, pp. 4-7.

Annex to the European Search Report for related Application No. EP05797894 dated Oct. 1, 2008.

Communication pursuant to Article 94(3) EPC issued Feb. 8, 2011 for European Patent Application No. 05 797 894.2—2112, which claims priority to PCT/US2005/033600 filed on Sep. 19, 2005 (Inventors—Karandikar et al.; Applicant—Acrymed, Inc.).

Acticoat RTM, Silver Coated Dressing Marketing Materials. The Westaim Corporation, 1988.

Bharathi, Subramanian et al., "Sol-Gel-Derived Nanocrystalline Gold-Silicate Composite Biosensor," Analytical Communications, 1998, 35: 29-31.

ConvaTec Corp. Aquacel Ag Product Info from website. [internet citation] Retrieved Dec. 9, 2002 from http://www.convatec.com/en_US/company/pr/index.html.

Deitch, E. et al., "Silver-Nylon: a New Antimicrobial Agent". Antimicrobial Agents and Chemotherapy, 1983, 23(3):356-359.

Deitch, E., et al., Abstract, "Silver-impregnated nylon cloth dressing: in vitro and in vivo evaluation of antimicrobial activity," J. Trauma, 1987, pp. 301-304, vol. 27, No. 3.

FDA Approval Letter to begin OxyGenesis marketing. Sep. 19, 2008.
Feng et al, "Study of the initiation mechanism of the vinyl polymerization with the system persulfate/N,N,N',N'-tetramethylethylenediamine," Makromol. Chem. 1988, 189: 77-83.

Gibbins et al., AcryDerm Absorbent Oxygen Dressing Point of Use Evaluation: Summary of Results. Draft. Jul. 17, 2009.

Gibbins, B. And Hopman, L., "A Comparison of a New Anti-Microbial Polyacrylate Absorbent Wound Dressing Containing Silver with the Silver-containing Anti-microbial Film Dressings", Presentation at Clinical Symposium on Wound Care, Oct. 2, 1999.

Jia et al., "Effect of locally released oxygen on wound healing," Presented at 18th Annual Meeting of the Wound Healing Society, San Diego, CA. Apr. 2008.

Junhui He et al, "Facile in situ synthesis of noble metal nanoparticles in porous cellulose fibers," Chemistry of Materials, 2003, 15(23): 4401-4406.

Kapoor, Sudhir, "Preparation, Characterization, and Surface Modification of Silver Particles," Langmuir, 1998, 14 (5):1021-1025.

MacKeen, P., et al., "Silver-Coated Nylon Fiber as an Antibacterial Agent," Antimicrobial Agents and Chemotherapy, 1987, 31(1): 93-99.

OxyGenesis Dissolved Oxygen Dressings: Case Review, AcryMed, Inc., Jan. 23, 2010.

Pepe, R.C, Wenninger, J.A., & McEwen, G.N., eds., Int'l Cosmetic Ingredient Dictionary & Handbook, 9th ed., 2002, vol. 2. pp. 177.

Rifai et al., "Facile in Situ Silver Nanoparticle Formation in Insulating Porous Polymer Matrices," Chemistry of Materials 2006; 18(1): 21-25.

Roe, David F., Gibbins, Bruce L., and Ladizinsky, Daniel A., "Topical Dissolved Oxygen Penetrates Skin: Model and Method," J Surg Res. 2010, 159(1):e29-e36.

Sheehan et al, "Anti-bacterial Silver Coatings on Orthopaedic Metals—An In Vitro and Animal Study," Journal of Bone and Joint Surgery. 2003, 85-B(SUPP_II):141.

Topical Delivery Methods, undated reference, retrieved from file on May 11, 2011.

(56) References Cited

OTHER PUBLICATIONS

Wang et al., "Directing oleate stabilized nanosized silver colloids into organic phases", Langmuir: The ACS Journal of Surfaces and Colloids. 1998; 14:602-610.

Communication regarding the expiration of opposition period issued on Feb. 10, 2006 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Decision to grant a European Pat. issued on Feb. 24, 2005 for European Pat. App. No. 98961733.7 which claims priority to PCT/US98/024272 filed on Nov. 13, 1998, published May 27, 1999, as WO 99/027680 (Applicant—Acrymed; Inventors: B.L. Gibbins).

Approval of request for amendments/corrections issued on Feb. 15, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Dec. 22, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Result of Consultation by telephone/in person (with time limit) issued on Nov. 9, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Request for correction/amendment of the text proposed for grant filed on Oct. 26, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication about intention to grant a European Pat. issued on Jun. 18, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Aug. 20, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication from the Examining Division issued on May 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on Feb. 5, 2003 for European Pat. App. No. 98961733.7 which claims priority to PCT/US98/024272 filed on Jan. 13, 1998, published May 27, 1999 as WO 99/027680 (Applicant—Acrymed; Inventors. B.L. Gibbins).

Communication from the Examining Division issued on Aug. 1, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Reply to communication from the Examining Division filed on May 20, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

Communication from the Examining Division issued Jul. 31, 2001 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).

PCT Intl. Search Report issued on Jun. 23, 1999 for PCT/US98/24272, filed on Nov. 13, 1998, published May 27, 1999 as WO 99/027680 (Applicant—Acrymed; Inventors: B.L. Gibbins).

PCT Intl. Preliminary exam report issued on Aug. 8, 2001 for PCT/US98/24272, filed on Nov. 13, 1998, published May 27, 1999 as WO 99/027680 (Applicant—Acrymed; Inventors: B.L. Gibbins).

PCT Written opinion issued on Feb. 18, 2000 for PCT/US98/24272, filed on Nov. 13, 1998, published May 27, 1999 as WO 99/027680 (Applicant—Acrymed; Inventors: B.L. Gibbins).

Issue Notification issued on Jul. 14, 1999 for U.S. Appl. No. 08/971,074, filed Nov. 14, 1997 (Inventor—B.L. Gibbins).

Notice of Allowance issued on Feb. 25, 1999 for U.S. Appl. No. 08/971,074, filed Nov. 14, 1997 (Inventor—B.L. Gibbins).

Examiner Interview Summary/Amendment issued on Dec. 11, 1998 for U.S. Appl. No. 08/971,074, filed Nov. 14, 1997 (Inventor—B.L. Gibbins).

Response after Non-Final Action filed on Nov. 18, 1998 for U.S. Appl. No. 08/971,074, filed Nov. 14, 1997 (Inventor—B.L. Gibbins).

Non-Final Rejection issued on Aug. 19, 1998 for U.S. Appl. No. 08/971,074, filed Nov. 14, 1997 (Inventor—B.L. Gibbins).

Response to Election / Restriction filed on Jul. 10, 1998 for U.S. Appl. No. 08/971,074, filed Nov. 14, 1997 (Inventor—B.L. Gibbins).

Restriction Requirement issued on May 21, 1998 for U.S. Appl. No. 08/971,074, filed Nov. 14, 1997 (Inventor—B.L. Gibbins).

Issue Notification issued on Mar. 12, 2002 for U.S. Appl. No. 09/191,223, filed Nov. 13, 1998 (Inventor—B.L. Gibbins).

Notice of Allowance issued on Sep. 25, 2001 for U.S. Appl. No. 09/191,223, filed Nov. 13, 1998 (Inventor—B.L. Gibbins).

Notice of Allowance issued on Oct. 3, 2000 for U.S. Appl. No. 09/191,223, filed Nov. 13, 2008 (Inventor—B.L. Gibbins).

Response after Non-Final Action filed on Aug. 11, 2000 for U.S. Appl. No. 09/191,223, filed Nov. 13, 1998 (Inventor—B.L. Gibbins).

Non-Final Rejection issued on Apr. 11, 2000 for U.S. Appl. No. 09/191,223, filed Nov. 13, 1998 (Inventor—B.L. Gibbins).

Response to Election / Restriction filed on Mar. 21, 2000 for U.S. Appl. No. 09/191,223, filed Nov. 13, 1998 (Inventor—B.L. Gibbins).

Restriction Requirement issued on Feb. 22, 2000 for U.S. Appl. No. 09/191,223, filed Nov. 13, 1998 (Inventor—B.L. Gibbins).

Communication regarding the expiry of opposition period issued on Sep. 2, 2009 for EP Appl. No. 970522.9, which claims priority to Intl. Pat. App. No. PCT/US00/26890, filed 9/29/200, published on Apr. 12, 2001 as WO 01/024839 (Applicant—Acrymed, Inc.).

Decision to grant a European Pat. issued on Oct. 2, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Communication about intention to grant a European Pat. issued on Apr. 10, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Reply to communication from the Examining Division filed on Feb. 26, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Communication from the Examining Division issued on Oct. 18, 2007 for Ep App. No. 970522.9, which claims priority to Intl. Pat. App. No. PCT/US00/26890, filed 9/29/200, published on Apr. 12, 2001 as WO 01/024839 (Applicant—Acrymed, Inc.).

Reply to communication from the Examining Division filed on Dec. 28, 2006 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Communication from the Examining Division issued on Sep. 1, 2006 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Reply to communication from the Examining Division filed on Mar. 21, 2005 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Communication from the Examining Division issued on Sep. 20, 2004 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

Reply to communication from the Examining Division filed on Feb. 27, 2003 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

(56) References Cited

OTHER PUBLICATIONS

Communication from the Examining Division issued on Aug. 21, 2002 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
PCT Intl. Search Report issued on Feb. 5, 2001 for PCT/US00/26890, filed on Sep. 29, 2000, published Apr. 12, 2001 as WO 01/24839 (Applicant—Acrymed; Inventors: Gibbins).
PCT Written Opinion issued on Jul. 23, 2001 for PCT/US00/26890, filed on Sep. 29, 2000, published Apr. 12, 2001 as WO 01/24839 (Applicant—Acrymed; Inventors: Gibbins).
PCT Intl. Preliminary Examination Report issued on Oct. 17, 2001 for PCT/US00/26890, filed on Sep. 29, 2000, published Apr. 12, 2001 as WO 01/24839 (Applicant—Acrymed; Inventors: Gibbins).
Notice of Allowance issued on Apr. 15, 2003 for U.S. Appl. No. 09/675,892, filed Sep. 29, 2000 (Inventor—B.L. Gibbins).
Amendment/Response After Non-Final Rejection filed on Mar. 21, 2003 for U.S. Appl. No. 09/675,892 filed Sep. 29, 2000 (Inventor—B.L. Gibbins).
Non-Final Rejection issued on Nov. 21, 2002 for U.S. Appl. No. 09/675,892, filed Sep. 29, 2000 (Inventor—B.L. Gibbins).
Amendment After Final filed on Oct. 30, 2002 for U.S. Appl. No. 09/675,892, filed Sep. 29, 2000 (Inventor—B.L. Gibbins).
Final Rejection issued on Jul. 31, 2002 for U.S. Appl. No. 09/675,892, filed Sep. 29, 2000 (Inventor—B.L. Gibbins).
Amendment/Response After Non-Final Rejection filed on Apr. 18, 2002 for U.S. Appl. No. 09/675,892, filed Sep. 29, 2000 (Inventor—B.L. Gibbins).
Non-Final Rejection issued on Jan. 18, 2002 for U.S. Appl. No. 09/675,892, filed Sep. 29, 2000 (Inventor—B.L. Gibbins).
Notice of Allowance issued on Mar. 7, 2005 for U.S. Appl. No. 10/441,275, filed May 19, 2003 (Inventor—B.L. Gibbins).
Notice of Allowance/Examiner Interview Summary Record issued on Jul. 2, 2004 for U.S. Appl. No. 10/441,275, filed May 19, 2003 (Inventor—B.L. Gibbins).
Examiner Interview Summary Record (PTOL—413) issued May 26, 2004 for U.S. Appl. No. 10/441,275, filed May 19, 2003 (Inventor—B.L. Gibbins).
Supplemental Preliminary Amendment filed on Mar. 25, 2004 for U.S. Appl. No. 10/441,275, filed May 19, 2003 (Inventor—B.L. Gibbins).
Preliminary Amendment filed on Dec. 2, 2003 for U.S. Appl. No. 10/441,275, filed May 19, 2003 (Inventor—B.L. Gibbins).
Issue Notification issued on Jul. 29, 2009 for U.S. Appl. No. 10/978,556, filed Nov. 1, 2004 (Inventor—B.L. Gibbins).
Notice of Allowance issued on Apr. 16, 2009 for U.S. Appl. No. 10/978,556, filed Nov. 1, 2004 (Inventor—B.L. Gibbins).
Terminal Disclaimer/Amendment After Final Rejection filed on Apr. 6, 2009 for U.S. Appl. No. 10/978,556, filed Nov. 1, 2004 (Inventor—B.L. Gibbins).
Final Rejection issued on Nov. 6, 2008 for U.S. Appl. No. 10/978,556, filed Nov. 1, 2004 (Inventor—B.L. Gibbins).
Amendment/Response After Non-Final Rejection filed on Aug. 1, 2008 for U.S. Appl. No. 10/978,556, filed Nov. 1, 2004 (Inventor—B.L. Gibbins).
Non-Final Rejection issued on Apr. 1, 2008 for U.S. Appl. No. 10/978,556, filed Nov. 1, 2004 (Inventor—B.L. Gibbins).
Amendment Submitted/Entered with CPA/RCE filed on Oct. 31, 2007 for U.S. Appl. No. 10/978,556, filed Nov. 1, 2004 (Inventor—B.L. Gibbins).
Advisory Action (PTOL-303) issued on Oct. 3, 2007 for U.S. Appl. No. 10/978,556, filed Nov. 1, 2004 (Inventor—B.L. Gibbins).
Amendment After Final Rejection filed on Sep. 13, 2007 for U.S. Appl. No. 10/978,556, filed Nov. 1, 2004 (Inventor—B.L. Gibbins).
Final Rejection issued on Jul. 13, 2007 for U.S. Appl. No. 10/978,556, filed Nov. 1, 2004 (Inventor—B.L. Gibbins).
Amendment/Response After Non-Final Rejection filed on Apr. 24, 2007 for U.S. Appl. No. 10/978,556, filed Nov. 1, 2004 (Inventor—B.L. Gibbins).
Non-Final Rejection issued on Jan. 24, 2007 for U.S. Appl. No. 10/978,556, filed Nov. 1, 2004 (Inventor—B.L. Gibbins).
Response to Election / Restriction filed on Nov. 13, 2006 for U.S. Appl. No. 10/978,556 filed Nov. 1, 2004 (Inventor—B.L. Gibbins).
Requirement for Restriction/Election issued on Oct. 11, 2006 for U.S. Appl. No. 10/978,556, filed Nov. 1, 2004 (Inventor—B.L. Gibbins).
Preliminary Amendment filed on Feb. 15, 2005 for U.S. Appl. No. 10/978,556, filed Nov. 1, 2004 (Inventor—B.L. Gibbins).
Reexamination Certificate Issued on Jun. 16, 2009 for Inter Partes Reexam U.S. Appl. No. 95/000,042 of U.S. Pat. No. 6,605,751 granted Aug. 12, 2003 (Gibbins et al.).
Notice of Intent to Issue a Reexam Certificate issued on Mar. 25, 2009 for Inter Partes Reexam U.S. Appl. No. 95/000,042 of U.S. Pat. No. 6,605,751 granted Aug. 12, 2003 (Gibbins et al.).
Right of Appeal Notice issued on Dec. 9, 2008 for Inter Partes Reexam U.S. Appl. No. 95/000,042 of U.S. Pat. No. 6,605,751 granted Aug. 12, 2003 (Gibbins et al.).
Action Closing Prosecution (nonfinal) issued on Aug. 19, 2008 for Inter Partes Reexam U.S. Appl. No. 95/000,042 of U.S. Pat. No. 6,605,751 granted Aug. 12, 2003 (Gibbins et al.).
Response after non-final action-owner filed on Oct. 8, 2004 for Inter Partes Reexam U.S. Appl. No. 95/000,042 of U.S. Pat. No. 6,605,751 granted Aug. 12, 2003 (Gibbins et al.).
Reexam Ordered and Non-Final Action issued on Aug. 4, 2004 for Inter Partes Reexam U.S. Appl. No. 95/000,042 of U.S. Pat. No. 6,605,751 granted Aug. 12, 2003 (Gibbins et al.).
Ex Parte Reexam request filed on May 13, 2004 for Inter Partes Reexam U.S. Appl. No. 95/000,042 of U.S. Pat. No. 6,605,751 granted Aug. 12, 2003 (Gibbins et al.).
Communication regarding the expiry of opposition period issued on Apr. 4, 2007 for EP App. No. 990393.1, which claims priority to PCT/US00/35560, filed on Dec. 29, 2000, published Jul. 12, 2001 as WO 01/49258 (Applicant—Acrymed).
Decision to grant a European Pat. issued on Apr. 21, 2006 for EP App. No. 990393.1, which claims priority to PCT/US00/35560, filed on Dec. 29, 2000, published Jul. 12, 2001 as WO 01/49258 (Applicant—Acrymed).
Reply to communication about intention to grant filed on Mar. 28, 2006 for EP App. No. 990393.1, which claims priority to PCT/US00/35560, filed on Dec. 29, 2000, published Jul. 12, 2001 as WO 01/49258 (Applicant—Acrymed).
Communication about intention to grant a European Pat. filed on Nov. 28, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Aug. 30, 2005 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 22, 2005 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Apr. 1, 2004 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 13, 2004 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Jul. 24, 2003 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Jan. 23, 2003 for EP App. No. 990393.1, which claims priority to PCT/US00/35560, filed on Dec. 29, 2000, published Jul. 12, 2001 as WO 01/49258 (Applicant—Acrymed).

(56) References Cited

OTHER PUBLICATIONS

Amendments before examination filed on Oct. 18, 2002 for Ep App. No. 990393.1, which claims priority to PCT/US00/35560, filed on Dec. 29, 2000, published Jul. 12, 2001 as WO 01/49258 (Applicant—Acrymed).
Amendments before examination filed on Jul. 19, 2002 for EP App. No. 990393.1, which claims priority to PCT/US00/35560, filed on Dec. 29, 2000, published Jul. 12, 2001 as WO 01/49258 (Applicant—Acrymed).
PCT Intl. Search Report issued on Jul. 12, 2001 for PCT/US00/35560, filed on Dec. 29, 2000, published Jul. 12, 2001 as WO 01/49258 (Applicant—Acrymed; Inventors: Gibbins).
PCT Intl. Preliminary Examination Report issued on Apr. 2, 2002 for PCT/US00/35560, filed on Dec. 29, 2000, published Jul. 12, 2001 as WO 01/49258 (Applicant—Acrymed; Inventors: Gibbins).
Non-Final Rejection mailed on Feb. 15, 2011 for U.S. Appl. No. 09/752,939, filed Dec. 29, 2000 (Inventor—Gibbins).
Amendment Submitted/Entered with CPA/RCE filed on Jan. 18, 2011 for U.S. Appl. No. 09/752,939, filed Dec. 29, 2000 (Inventor—Gibbins).
Notice of Appeal filed on Jun. 17, 2010 for U.S. Appl. No. 09/752,939, filed Dec. 29, 2000 (Inventor—Gibbins).
Final Rejection issued on Feb. 25, 2010 for U.S. Appl. No. 09/752,939, filed Dec. 29, 2000 (Inventor—Gibbins).
Amendment/Response After Non-Final Action filed on Dec. 3, 2009 for U.S. Appl. No. 09/752,939, filed Dec. 29, 2000 (Inventor—Gibbins).
Non-Final Rejection issued on Jun. 4, 2009 for U.S. App. No. 09/752,939, filed Dec. 29, 2000 (Inventor—Gibbins).
Amendment Submitted/Entered with CPA/RCE filed on Mar. 16, 2009 for U.S. Appl. No. 09/752,939, filed Dec. 29, 2000 (Inventor—Gibbins).
Final Rejection issued on Sep. 18, 2008 for U.S. Appl. No. 09/752,939, filed Dec. 29, 2000 (Inventor—Gibbins).
Amendment/Response After Non-Final Action filed on Apr. 28, 2008 for U.S. Appl. No. 09/752,939, filed Dec. 29, 2000 (Inventor—Gibbins).
Non-Final Rejection issued on Dec. 28, 2007 for U.S. Appl. No. 09/752,939, filed Dec. 29, 2000 (Inventor—Gibbins).
Amendment Submitted/Entered with CPA/RCE filed on Oct. 9, 2007 for U.S. Appl. No. 09/752,939 filed Dec. 29, 2000 (Inventor—Gibbins).
Advisory Action (PTOL-303) issued on Sep. 4, 2007 for U.S. Appl. No. 09/752,939, filed Dec. 29, 2000 (Inventor—Gibbins).
Amendment After Final Rejection filed on Aug. 6, 2007 for U.S. Appl. No. 09/752,939, filed Dec. 29, 2000 (Inventor—Gibbins).
Final Rejection issued on Jun. 6, 2007 for U.S. Appl. No. 09/752,939, filed Dec. 29, 2000 (Inventor—Gibbins).
Supplemental Response/Amendment filed on Apr. 3, 2007 for U.S. Appl. No. 09/752,939, filed Dec. 29, 2000 (Inventor—Gibbins).
Amendment/Response After Non-Final Action filed on Feb. 14, 2007 for U.S. Appl. No. 09/752,939, filed Dec. 29, 2000 (Inventor—Gibbins).
Examiner Interview Summary Record (PTOL—413) issued on Jan. 17, 2007 for U.S. Appl. No. 09/752,939, filed Dec. 29, 2000 (Inventor—Gibbins).
Non-Final Rejection issued on Sep. 14, 2006 for U.S. Appl. No. 09/752,939, filed Dec. 29, 2000 (Inventor—Gibbins).
Amendment Submitted/Entered with CPA/RCE filed on Aug. 7, 2006 for U.S. Appl. No. 09/752,939, filed Dec. 29, 2000 (Inventor—Gibbins).
Amendment initialed by Examiner/Advisory Action (PTOL—303) issued on May 18, 2006 for U.S. Appl. No. 09/752,939, filed Dec. 29, 2000 (Inventor—Gibbins).
Amendment After Final Rejection filed on May 8, 2006 for U.S. Appl. No. 09/752,939, filed Dec. 29, 2000 (Inventor—Gibbins).
Final Rejection issued on Mar. 7, 2006 for U.S. Appl. No. 09/752,939, filed Dec. 29, 2000 (Inventor—Gibbins).
Amendment/Response After Non-Final Action filed on Dec. 1, 2005 for U.S. App. No. 09/752,939, filed Dec. 29, 2000 (Inventor—Gibbins).
Non-Final Rejection issued on Aug. 2, 2005 for U.S. Appl. No. 09/752,939, filed Dec. 29, 2000 (Inventor—Gibbins).
Amendment Submitted/Entered with CPA/RCE filed on Jun. 15, 2005 for U.S. Appl. No. 09/752,939, filed Dec. 29, 2000 (Inventor—Gibbins).
Advisory Action (PTOL—303) issued on Jun. 8, 2005 for U.S. Appl. No. 09/752,939, filed Dec. 29, 2000 (Inventor—Gibbins).
Amendment After Final Rejection filed on Mar. 30, 2005 for U.S. Appl. No. 09/752,939, filed Dec. 29, 2000 (Inventor—Gibbins).
Final Rejection issued on Dec. 16, 2004 for U.S. Appl. No. 09/752,939, filed Dec. 29, 2000 (Inventor—Gibbins).
Amendment/Response After Non-Final Action filed on Sep. 16, 2004 for U.S. Appl. No. 09/752,939, filed Dec. 29, 2000 (Inventor—Gibbins).
Non-Final Rejection issued on May 17, 2004 for U.S. Appl. No. 09/752,939, filed Dec. 29, 2000 (Inventor—Gibbins).
Decision to Withdraw from Issue issued on Apr. 26, 2004 for U.S. Appl. No. 09/752,939, filed Dec. 29, 2000 (Inventor—Gibbins).
Notice of Allowance issued on Jan. 23, 2003 for U.S. Appl. No. 09/752,939, filed Dec. 29, 2000 (Inventor—Gibbins).
Amendment Submitted/Entered with CPA/RCE filed on Nov. 15, 2002 for U.S. Appl. No. 09/752,939, filed Dec. 29, 2000 (Inventor—Gibbins).
Advisory Action (PTOL—303) issued on Nov. 19, 2002 for U.S. Appl. No. 09/752,939 filed Dec. 29, 2000 (Inventor—Gibbins).
Amendment After Final Rejection filed on Oct. 15, 2002 for U.S. Appl. No. 09/752,939, filed Dec. 29, 2000 (Inventor—Gibbins).
Final Rejection issued on Jul. 15, 2002 for U.S. Appl. No. 09/752,939, filed Dec. 29, 2000 (Inventor—Gibbins).
Amendment/Response After Non-Final Action filed on Apr. 18, 2002 for U.S. Appl. No. 09/752,939, filed Dec. 29, 2000 (Inventor—Gibbins).
Examiner Interview Summary Record (PTOL—413) issued on Apr. 11, 2002 for U.S. Appl. No. 09/752,939, filed Dec. 29, 2000 (Inventor—Gibbins).
Non-Final Rejection issued on Dec. 18, 2001 for for U.S. Appl. No. 09/752,939, filed Dec. 29, 2000 (Inventor—Gibbins).
Issue Notification issued on Dec. 20, 2006 for U.S. Appl. No. 10/441,141, filed May 19, 2003 (Inventor—Gibbins).
Notice of Allowance/Examiner Interview Summary Record (PTOL—413) issued on Jul. 25, 2006 for U.S. Appl. No. 10/441,141, filed May 19, 2003 (Inventor—Gibbins).
Amendment After Final Rejection filed on Jul. 5, 2006 for U.S. Appl. No. 10/441,141, filed May 19, 2003 (Inventor—Gibbins).
Examiner Interview Summary Record (PTOL—413) issued on Jun. 28, 2006 for U.S. Appl. No. 10/441,141, filed May 19, 2003 (Inventor—Gibbins).
Final Rejection issued on May 4, 2006 for U.S. Appl. No. 10/441,141, filed May 19, 2003 (Inventor—Gibbins).
Amendment/Response After Non-Final Action filed on Feb. 14, 2006 for U.S. Appl. No. 10/441,141 filed May 19, 2003 (Inventor—Gibbins).
Non-Final Rejection issued on Nov. 15, 2005 for U.S. Appl. No. 10/441,141, filed May 19, 2003 (Inventor—Gibbins).
Preliminary Amendment filed on Apr. 12, 2003 for U.S. Appl. No. 10/441,141, filed May 19, 2003 (Inventor—Gibbins).
Notification of Grant issued Feb. 5, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fifth Office Action filed on Jan. 7, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.) + claims in English.
Fifth Office Action issued on Oct. 23, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fourth Office Action filed on Sep. 11, 2009 for Chinese Pat. App. No. 03820077.5, which claims priority to PCT/US03/

(56) References Cited

OTHER PUBLICATIONS 023851 filed Jul. 29, 2003, published Feb. 5, 2004 as WO 04/010952 (Applicant—Acrymed, Inc.)—English translation only.
Fourth Office Action issued on Apr. 17, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to third Office Action filed on Aug. 27, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.) claims in English.
Third Office Action issued on Jun. 13, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to Second Office Action filed on Dec. 25, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
Second Office Action issed for Aug. 10, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to first Office Action filed on Sep. 1, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
First Office Action issued on Apr. 21, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Decision to Grant pursuant to Article 97(2) EPC issued on Dec. 2, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication under Rule 71(3) EPC issued on Jun. 4, 2010 for EP App. No. 3772113.1, which claims priority to PCT/US03/023851 filed Jul. 29, 2003, published Feb. 5, 2004 as WO 04/010952 (Applicant—Acrymed, Inc.).
Letter during examination procedure after communication from the Examining Division filed on Jan. 19, 2010 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jan. 13, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division issued on Jul. 3, 2009 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jul. 15, 2008 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division issued on Jan. 10, 2008 for EP App. No. 3772113.1, which claims priority to PCT/US03/023851 filed Jul. 29, 2003, published Feb. 5, 2004 as WO 04/010952 (Applicant—Acrymed, Inc.).
Supplementary European search report issued on Dec. 14, 2006 for EP App. No. 3772113.1, which claims priority to PCT/US03/023851 filed Jul. 29, 2003, published Feb. 5, 2004 as WO 04/010952 (Applicant—Acrymed, Inc.).
Preliminary Amendment filed on Apr. 12, 2005 for EP App. No. 3772113.1, which claims priority to PCT/US03/023851 filed Jul. 29, 2003, published Feb. 5, 2004 as WO 04/010952 (Applicant—Acrymed, Inc.).

PCT Intl. Search Report issued on Aug. 27, 2004 for Intl. App. No. PCT/US03/023851 filed Jul. 29, 2003, published Feb. 5, 2004 as WO 04/010952 (Applicant—AcryMed, Inc.).
Issue Notification issued on Jul. 6, 2005 for U.S. Appl. No. 10/207,936, filed Jul. 29, 2002 (Inventor—Maley, J. C.).
Amendment/Response-After Non-Final Rejection filed on Apr. 25, 2005 for U.S. Appl. No. 10/207,936, filed Jul. 29, 2002 (Inventor—Maley, J. C.).
Office Communication issued on Mar. 30, 2005 for U.S. Appl. No. 10/207,936 filed Jul. 29, 2002 (Inventor—Maley, J. C.).
Notice of Allowance and Fees Due (PTOL—85) with Examiner Interview Summary Record (PTOL—413) issued Feb. 16, 2005 for U.S. Appl. No. 10/207,936, filed Jul. 29, 2002 (Inventor—Maley, J. C.).
Supplemental Amendment after Final Rejection issued on Jan. 28, 2005 for U.S. Appl. No. 10/207,936, filed Jul. 29, 2002 (Inventor—Maley, J. C.).
Amendment After Final Rejection filed on Jan. 12, 2005 for U.S. Appl. No. 10/207,936, filed Jul. 29, 2002 (Inventor—Maley, J. C.).
Final Rejection issued on Nov. 23, 2004 for U.S. Appl. No. 10/207,936, filed Jul. 29, 2002 (Inventor—Maley, J. C.).
Response After Non-Final Rejection filed on Jul. 29, 2004 for U.S. Appl. No. 10/207,936, filed Jul. 29, 2002 (Inventor—Maley, J. C.).
Non-Final Rejection issued on Apr. 29, 2004 for U.S. Appl. No. 10/207,936, filed Jul. 29, 2002 (Inventor—Maley, J. C.).
Response After Non-Final Rejection filed on Jan. 22, 2004 for U.S. Appl. No. 10/207,936, filed Jul. 29, 2002 (Inventor—Maley, J. C.).
Non-Final Rejection issued on Oct. 22, 2003 for U.S. Appl. No. 10/207,936, filed Jul. 29, 2002 (Inventor—Maley, J. C.).
Response After Non-Compliant Amendment filed on Jun. 2, 2010 for U.S. Appl. No. 10/630,627, filed Jul. 29, 2003 (Inventor—Maley, J.C.).
Amendment Submitted/Entered with CPA/RCE filed on Apr. 27, 2010 for U.S. Appl. No. 10/630,627, filed Jul. 29, 2003 (Inventor—Maley, J.C.).
Final Rejection issued on Dec. 3, 2009 for U.S. Appl. No. 10/630,627, filed Jul. 29, 2003 (Inventor—Maley, J.C.).
Response After Non-Final Rejection filed on Jul. 20, 2009 for U.S. Appl. No. 10/630,627, filed Jul. 29, 2003 (Inventor—Maley, J.C.).
Non-Final Rejection issued on Feb. 19, 2009 for U.S. Appl. No. 10/630,627, filed Jul. 29, 2003 (Inventor—Maley, J.C.).
Amendment Submitted/Entered with CPA/RCE filed on Nov. 26, 2008 for U.S. Appl. No. 10/630,627, filed Jul. 29, 2003 (Inventor—Maley, J.C.).
Final Rejection issued on Jun. 26, 2008 for U.S. Appl. No. 10/630,627, filed Jul. 29, 2003 (Inventor—Maley, J.C.).
Response After Non-Final Rejection filed on Feb. 7, 2008 for U.S. Appl. No. 10/630,627, filed Jul. 29, 2003 (Inventor—Maley, J.C.).
Non-Final Rejection issued on Sep. 7, 2007 for U.S. Appl. No. 10/630,627, filed Jul. 29, 2003 (Inventor—Maley, J.C.).
Amendment Submitted/Entered with CPA/RCE filed on Jun. 22, 2007 for U.S. Appl. No. 10/630,627, filed Jul. 29, 2003 (Inventor—Maley, J.C.).
Advisory Action (PTOL—303) issued on May 17, 2007 for U.S. Appl. No. 10/630,627, filed Jul. 29, 2003 (Inventor—Maley, J.C.).
Amendment After Final Rejection filed on Apr. 23, 2007 for U.S. Appl. No. 10/630,627, filed Jul. 29, 2003 (Inventor—Maley, J.C.).
Final Rejection issued on Feb. 23, 2007 for U.S. Appl. No. 10/630,627, filed Jul. 29, 2003 (Inventor—Maley, J.C.).
Response After Non-Final Rejection filed on Nov. 21, 2006 for U.S. Appl. No. 10/630,627, filed Jul. 29, 2003 (Inventor—Maley, J.C.).
Non-Final Rejection issued on Aug. 24, 2006 for U.S. Appl. No. 10/630,627, filed Jul. 29, 2003 (Inventor—Maley, J.C.).
Response to Election / Restriction Filed on Jun. 23, 2006 for U.S. Appl. No. 10/630,627, filed Jul. 29, 2003 (Inventor—Maley, J.C.).
Restriction/Election Requirement issued on May 23, 2006 for U.S. Appl. No. 10/630,627, filed Jul. 29, 2003 (Inventor—Maley, J.C.).
Second Office Action issued on Aug. 12, 2011 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Response to First Office Action filed on Jul. 9, 2009 for Chinese Pat. App. No. 200580028750.9, which claims priority to Intl. App. No.

(56) References Cited

OTHER PUBLICATIONS

PCT/US/05/027260 filed Aug. 1, 2005, published Feb. 9, 2006 as WO 06/015317 (Applicant—Acrymed, Inc.)—Proposed Claims in English.
First Office Action issued on Dec. 26, 2008 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Amended claims filed on Feb. 26, 2007 for EP App. No. 05778379.7, which claims priority to Intl. App. No. PCT/US05/027260 filed Aug. 1, 2005, published Feb. 9, 2006 as WO 06/015317 (Applicant—Acrymed, Inc.).
Response to Examiner's Report filed on Jun. 29, 2011 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Examiner's Report issued on Jun. 29, 2010 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Intl. Preliminary Report on Patentability issued on Jan. 30, 2007 for Intl. App. No. PCT/US05/027260 filed Aug. 1, 2005, published Feb. 9, 2006 as WO 06/015317 (Applicant—Acrymed, Inc.).
Intl. Search Report with Written Opinion issued on Apr. 28, 2006 for Intl. App. No. PCT/US05/027260 filed Aug. 1, 2005, published Feb. 9, 2006 as WO 06/015317 (Applicant—Acrymed, Inc.).
Protest Documents from 3rd Party filed on Apr. 3, 2009 for U.S. Appl. No. 11/572,899, filed May 13, 2008 (Inventor—Karandikar et al.).
Preliminary Amendment filed on Jan. 29, 2007 for U.S. Appl. No. 11/572,899, filed May 13, 2008 (Inventor—Karandikar et al.).
Intl. Preliminary Report on Patentability issued on Jan. 30, 2007 for Intl. App. No. PCT/US05/027261 filed Aug. 1, 2005, published Mar. 9, 2006 as WO 06/026026 (Applicant—Acrymed, Inc.).
Intl. Search Report with Written Opinion issued on Apr. 28, 2006 for Intl. App. No. PCT/US05/027261 filed Aug. 1, 2005, published Mar. 9, 2006 as WO 06/026026 (Applicant—Acrymed, Inc.).
Notice of Acceptance issued on Jan. 24, 2011 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Dec. 13, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Examiners First Report issued on Feb. 19, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
AU Divisional App. No. 2011202034 filed on May 3, 2011 from AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Second Office Action (Text Portion) issued on Jun. 7, 2011 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Office Action filed on Jul. 9, 2009 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
First Office Action issued on Dec. 26, 2008 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Jun. 30, 2011 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.)—proposed amendments only.
Examiner's Report issued on Jul. 2, 2010 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.).
Official Action issued on Mar. 1, 2011 for JP App. No. 2007-523881, which claims priority to Intl. Pat. App. No. PCT/US05/027261, filed on Aug. 1, 2005, published on Mar. 9, 2006 as WO 06/02026 (Applicant—Acrymed, Inc.)—translation included.
Notice of Acceptance issued on Apr. 26, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Apr. 21, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Feb. 2, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Jan. 20, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Further Examination Report issued on Jul. 8, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response and Amended Pages filed on Jun. 28, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Apr. 24, 2009 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
NZ Divisional App. No. 592438 filed on Apr. 21, 2011 from New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examiner's first report issued on Oct. 18, 2010 for Australian Pat. App. No. 2007215443, which claims priority to PCT/US07/03390, filed Feb. 8, 2007, published on Aug. 23, 2007 as WO 07/095058 (Applicant—Acrymed, Inc.).
Response to Second Office Action filed on Jun. 7, 2011 for Chinese Pat. App. No. 200780012684.5, which claims priority to PCT/US07/003390 filed on Feb. 8, 2007 (Applicant—AcryMed, Inc.)—No Translation.
Second Office Action issued Mar. 23, 2011 for Chinese Pat. App. No. 200780012684.5, which claims priority to PCT/US07/003390 filed on Feb. 8, 2007 (Applicant—AcryMed, Inc.).
Response to First Office Action filed on Feb. 28, 2011 for Chinese Pat. App. No. 200780012684.5, which claims priority to PCT/US07/003390 filed on Feb. 8, 2007 (Applicant—AcryMed, Inc.)—Proposed amended claims in English.
First Office Action issued Oct. 13, 2010 for Chinese Pat. App. No. 200780012684.5, which claims priority to PCT/US07/003390 filed on Feb. 8, 2007 (Applicant—AcryMed, Inc.).
Claim amendments filed on Sep. 4, 2008 for EP App. No. 07750244.1, which claims priority to PCT/US07/03390, filed Feb. 8, 2007, published on Aug. 23, 2007 as WO 07/095058 (Applicant—Acrymed, Inc.).
PCT Preliminary Report on Patentability issued on Aug. 12, 2008 for Intl. Pat. App. No. PCT/US07/03390, filed Feb. 8, 2007, published on Aug. 23, 2007 as WO 07/095058 (Applicant—Acrymed, Inc.).
PCT Intl. Search Report with Written Opinion issued on Dec. 21, 2007 for Intl. Pat. App. No. PCT/US07/03390, filed Feb. 8, 2007, published on Aug. 23, 2007 as WO 07/095058 (Applicant—Acrymed, Inc.).
Amendment Entered with CPA/RCE filed on Apr. 22, 2011 for U.S. Appl. No. 11/704,167, filed Feb. 8, 2007 (Inventors—Karandikar et al.).

(56) References Cited

OTHER PUBLICATIONS

Final Rejection issued on Dec. 22, 2010 for U.S. Appl. No. 11/704,167, filed Feb. 8, 2007 (Inventors—Karandikar et al.).
Response after Non-Final Action mailed Oct. 28, 2010 for U.S. Appl. No. 11/704,167, filed Aug. 2, 2007 (Inventors—Karandikar et al.).
Non-Final Rejection issued on May 28, 2010 for U.S. Appl. No. 11/704,167, filed Feb. 8, 2007 (Inventors—Karandikar et al.).
Response to Election / Restriction filed on Apr. 30, 2010 for U.S. Appl. No. 11/704,167, filed Aug. 2, 2007 (Inventors—Karandikar et al.).
Restriction/Election Requirement issued on Mar. 30, 2010 for U.S. Appl. No. 11/704,167, filed Feb. 8, 2007 (Inventors—Karandikar et al.).
Preliminary Amendments filed on Nov. 24, 2008 for EP 07755996.1 which claims priority to PCT/US07/009997, filed on Apr. 25, 2007, published on Nov. 8, 2007 as WO 07/127236 (Applicant—Acrymed, Inc.).
Intl. Search Report w/ Written Opinion issued on Aug. 25, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability issued on Oct. 28, 2008 for Intl. Pat. App. No. PCT/US07/009997, filed on Apr. 25, 2007, published on Nov. 8, 2007 as WO 07/127236 (Applicant—Acrymed, Inc.).
Final Rejection issued on Jun. 23, 2011 for U.S. Appl. No. 11/789,701, filed Apr. 25, 2007 (Inventors—McMaken et al.).
Response after Non-Final Rejection filed on Apr. 5, 2011 for U.S. Appl. No. 11/789,701, filed Apr. 25, 2007 (Inventors—McMaken et al.).
Non-Final Rejection issued on Oct. 5, 2010 for U.S. Appl. No. 11/789,701, filed Apr. 25, 2007 (Inventors—McMaken et al.).
Amendment Entered with CPA/RCE filed on Mar. 31, 2010 for U.S. Appl. No. 11/789,701, filed Apr. 25, 2007 (Inventors—McMaken et al.).
Final Rejection issued on Oct. 5, 2009 for U.S. Appl. No. 11/789,701, filed Apr. 25, 2007 (Inventors—McMaken et al.).
Response After Non-Final Rejection filed Jun. 8, 2009 for U.S. Appl. No. 11/789,701, filed Apr. 25, 2007 (Inventors—McMaken et al.).
Non-Final Rejection issued on Jan. 26, 2009 for U.S. Appl. No. 11/789,701, filed Apr. 25, 2007 (Inventors—McMaken et al.).
Response to Election / Restriction filed on Dec. 15, 2008 for U.S. Appl. No. 11/789,701, filed Apr. 25, 2007 (Inventors—McMaken et al.).
Requirement for Restriction/Election issued on Nov. 14, 2008 for U.S. Appl. No. 11/789,701, filed Apr. 25, 2007 (Inventors—McMaken et al.).
Intl. Preliminary Report on Patentability issued on May 24, 2011 for Intl. Pat. App. No. PCT/US09/065764, filed on Nov. 24, 2009, published on May 27, 2010 as WO 10/060094 (Applicant—Kimberly-Clark, Worldwide Inc..).
Intl. Search Report with Written Opinion issued on Apr. 28, 2010 for Intl. Pat. App. No. PCT/US09/065764, filed on Nov. 24, 2009, published on May 27, 2010 as WO 10/060094 (Applicant—Kimberly-Clark, Worldwide Inc.).
Communication from Examining Division filed on Jun. 16, 2011 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Feb. 8, 2011 for EP App. No. 05797894.2, which claims priority to PCT/US05/033600, filed Sep. 19, 2005, published on Mar. 30, 2006 as WO 06/034249 (Applicant—Acrymed, Inc.).
Amendments before examination filed on Apr. 18, 2007 for EP App. No. 05797894.2, which claims priority to PCT/US05/033600, filed Sep. 19, 2005, published on Mar. 30, 2006 as WO 06/034249 (Applicant—Acrymed, Inc.).
Third Office Action issued Jul. 7, 2011 for Chinese Pat. App. No. 200780012684.5, which claims priority to PCT/US07/003390 filed on Feb. 8, 2007 (Applicant—AcryMed, Inc.).
Non-Final Rejection issued on Jun. 28, 2011 for U.S. Appl. No. 10/630,627, filed Jul. 29, 2003 (Inventor—Maley, J.C.).
Notice of Allowance issued on May 12, 2011 for U.S. Appl. No. 12/510,651, filed Jul. 28, 2009 (Inventor—Gibbins).
Amendment/Response After Non-Final Reject/Terminal Disclaimer filed on Apr. 4, 2011 for U.S. Appl. No. 12/510,651, filed Jul. 28, 2009 (Inventor—Gibbins).
Non-Final Rejection issued on Jan. 5, 2011 for U.S. Appl. No. 12/510,651, filed Jul. 28, 2009 (Inventor—Gibbins).
Preliminary Amendment filed on Oct. 28, 2009 for U.S. Appl. No. 12/510,651, filed Jul. 28, 2009 (Inventor—Gibbins).
Response to Restriction Requirement filed on Aug. 9, 2011 for U.S. Appl. No. 11/572,899, filed May 13, 2008 (Inventor—Karandikar et al.).
Restriction requirement issued on Jun. 28, 2011 for U.S. Appl. No. 11/572,899, filed May 13, 2008 (Inventor—Karandikar et al.).
Supplemental European Search Report issued May 23, 2011 for EP App. No. 07750244.1, which claims priority to PCT/US07/03390, filed Feb. 8, 2007, published on Aug. 23, 2007 as WO 07/095058 (Applicant—Acrymed, Inc.).
Non-Final Rejection issued on Jun. 30, 2011 for U.S. Appl. No. 11/704,167, filed Feb. 8, 2007 (Inventors—Karandikar et al.).
Amendment/Response After Non-Final Action filed on Aug. 9, 2011 for U.S. Appl. No. 09/752,939, filed Dec. 29, 2000 (Inventor—Gibbins).
Non-Final Rejection issued on Aug. 17, 2011 for U.S. Appl. No. 12/510,651, filed on Jul. 28, 2009 (Inventor—Gibbins).
Response after Non-Final Rejection filed on Aug. 26, 2011 for U.S. Appl. No. 12/510,651, filed on Jul. 28, 2009 (Inventor—Gibbins).
Amendment Entered with CPA/RCE filed on Feb. 19, 2010 for U.S. Appl. No. 11/194,951, filed Aug. 1, 2005 (Inventor—Karandikar et al.).
Notice of Appeal filed on Oct. 21, 2009 for U.S. Appl. No. 11/194,951, filed Aug. 1, 2005 (Inventor—Karandikar et al.).
Final Rejection issued on May 21, 2009 for U.S. App. No. 11/194,951, filed Aug. 1, 2005 (Inventor—Karandikar et al.).
Response After Non-Final Rejection filed on Feb. 5, 2009 for U.S. Appl. No. 11/194,951, filed Aug. 1, 2005 (Inventor—Karandikar et al.).
Non-Final Rejection issued on Aug. 5, 2008 for U.S. Appl. No. 11/194,951, filed Aug. 1, 2005 (Inventor—Karandikar et al.).
Response to Election / Restriction filed on Feb. 5, 2008 for U.S. Appl. No. 11/194,951, filed Jan. 8, 2005 (Inventor—Karandikar et al.).
Requirement for Restriction/Election issued on Dec. 5, 2007 for U.S. Appl. No. 11/194,951, filed Aug. 1, 2005 (Inventor—Karandikar et al.).
Article—Wagner et al, "Characterization of Silver Anthranilate, a Promising Antibacterial Agent," *Acta Farm. Bonaerense*, vol. 21, No. 1, 2002, pp. 27-30.
Liz-Marzán et al., "Reduction and Stabilization of Silver Nanoparticles in Ethanol by Nonionic Surfactants," *Langmuir*, vol. 12, 1996, pp. 3585-3589.
Pastoriza-Santos et al., "Reduction of silver nanoparticles in DMF. Formation of monolayers and stable colloids*," *Pure Appl. Chem.*, vol. 72, Nos. 1-2, 2000, pp. 83-90.

\* cited by examiner

ANTIMICROBIAL AMORPHOUS COMPOSITIONS

RELATED APPLICATIONS

This application is a national stage application of PCT/US2005/033600 filed Sep. 19, 2005, which claims the priority of U.S. Provisional Patent Application Ser. No. 60/611,486, filed Sep. 20, 2004, each of which is incorporated herein in its entirety.

FIELD OF THE INVENTION

The invention pertains to compositions comprising stabilized silver in amorphous formulations, and methods of making and using such compositions.

BACKGROUND OF THE INVENTION

Silver has been long recognized for its antimicrobial properties. It was shown in the late 19$^{th}$ century that the ionic state of silver was the only form of silver that possessed this property (Ravelin, J. Sci. Nat. Vol. 11, p 93-102, 1869). It was subsequently shown that only minute amounts of silver are needed to demonstrate the antimicrobial effect (van Naegeli, V., Deut. Schr. Schweiz. Naturforsch. Ges., Vol. 33, p 174-182, 1893). The predominant forms of silver are in one of two oxidation states. The reduced form of silver is the metallic form commonly found in ornaments and jewelry. This form possesses no antimicrobial properties. The other common form is the oxidized ionic state also known as $Ag^+$ which is the antimicrobial form of silver. $Ag^+$ as the free ion is unstable and is almost always found in a complex with negatively charged elements or compounds. Ionic silver bound to these negatively charged groups often disrupts normal function and is commonly cited as the explanation of the mode of action of silver (Hugo, W. B. and A. D. Russell, Prog. Med. Chem., Vol. 31, p 351-368, 1994). These negatively charged side groups are common to the macromolecular structures of virtually all microorganisms which makes the organisms susceptible to the antimicrobial action of this element. Thus, silver is known as a broad spectrum antimicrobial agent.

The broad spectrum action of silver has been exploited in medical applications. Solutions of ionic silver have been used for more than 100 years for the prevention of neonate opthalmia (congenital blindness) caused by the organism responsible for gonorrhea. Ionic silver solutions have also been used for the control of bacterial infections in serious burn injuries. Although effective, it has been found that ionic silver has a very short half life or time in which it is available to attack bacteria. Tissue components including proteins and various anions in body fluids bind to silver and reduce its availability for acting on bacteria.

Another problem encountered with silver is its reaction to light. Ionic silver and salts of silver react to light energy which causes profound changes in color. An example is the photoreduction of ionic silver, often seen as a blackening or dark staining of surfaces in contact with silver solutions. An attempt to overcome this problem of light instability was the development of the compound silver sulfadiazine (Fox, C. J., Arch. Surg., Vol. 96, p 184-188, 1968) where ionic silver was bound to sulfadiazine and delivered in an oil and water emulsion. Although this delivery vehicle of silver overcame some of the light instability issues, it still has limitations. Silver sulfadiazine, for example, is currently sold as Silvadene, (Marion Boots), its activity rapidly decays in a wound environment. The material is largely an oil-based product that stains bedding and clothing. Moreover, many patients develop allergic reactions to the sulfadiazine moiety of the product.

The control of bioburden in the wound environment has long been practiced by wound care providers. However modern wound care coverings that maintain conditions that optimize wound healing typically out last the activity of antimicrobial agents applied to the wound during dressing changes. This results in the undesirable situation where moist wound management is used to encourage tissue proliferation and repair without protection against microbial growth. Indeed the conditions that encourage tissue growth also are typically optimal conditions for microbial growth.

To overcome this limitation, manufacturers have attempted to incorporate agents into dressing materials so that there is coincident application of an antimicrobial agent along with the use of absorbent moisture management wound contact materials. Some products combine the antimicrobial, iodine, with a hydrophilic polymer for control of wound exudate and bioburden (Iodosorb and Iodoflex, Healthpoint Medical, Fort Worth Tex.). However iodine is relatively toxic at the 10,000 ppm level that is present in such products. Other wound care products utilize stabilized silver chloride in hydrophilic matrices (SilvaSorb, Medline Mundelein Il, Aquacel Ag Convatec, Skillman N.J.). Although effective in controlling bioburden, these products are useful on wounds where fluids are present so as to mobilize the silver ions. However not all wounds are sufficiently moist to enable mobilization of silver for the purpose of causing an antimicrobial effect in the wound environment. In these cases it is necessary to add the moisture. Although hydrating gels are marketed, none of them provide adequate antimicrobial protection to control the bioburden in the wound environment.

There is a need for antimicrobial wound care devices and compositions in the form of a spreadable amorphous formulation.

SUMMARY OF THE INVENTION

The present invention comprises methods and compositions for treatment of conditions related to loss of integrity by organs, such as the skin, or other sites where an antimicrobial environment is desired. In general, the present invention comprises compositions comprising silver compounds provided to sites of loss of integrity such as wounds, burns, abrasions, breaks, tears, cuts or surgical sites, or to sites where bacteria are not desired, such as insertion sites of catheters, lubrication of catheters, or oral buccal disinfection. An aspect of the present invention comprises a compound of which ionic silver is a component, and delivery of that compound using an amorphous composition. The amorphous compositions are generally spreadable, for application on a desired site, thus providing uniform coverage to maximize delivery of the antimicrobial activity to the intended site.

Aspects of the invention comprise compositions comprising stabilized silver antimicrobial compositions in an amorphous formulation delivery vehicle to form stabilized silver antimicrobial compositions. Such compositions have utility in topical applications. The silver composition may be formed from the combination of at least two solutions, one solution comprising a silver cation and another solution comprising an anion, from which the combination of the two solutions, in no particular order, form a weakly soluble salt of silver. The silver composition may be made and then added to the amorphous delivery composition, or it may be made by sequentially adding the solutions necessary to form the silver composition directly to the amorphous delivery composition, or to components of the amorphous delivery composition. Stabilizing agents, oxidizing agents or other compositions or solutions may be added at various steps, such as in the formation of the silver composition, in the formation of the amorphous delivery composition, to both solutions (cationic or anionic solutions) or after the combination of the silver salt composition and the amorphous delivery vehicle composition, or after formation of the silver salt composition in the amorphous delivery composition. Other optional components may also be added, including, but not limited to active agents and surfactants.

Aspects of the methods of the present invention comprise making and using the compositions taught herein. For example, the compositions may be used in treating conditions relating to loss of skin or organ integrity comprising, applying an antimicrobial composition comprising an amorphous delivery vehicle admixed with a stabilized silver salt composition.

DETAILED DESCRIPTION

The present invention comprises methods and compositions for treatments of conditions related to loss of organ integrity, such as wound care, and also the provision of antimicrobial conditions to environments where bacterial contamination is unwanted. The present invention comprises compositions comprising amorphous compositions containing stabilized ionic silver. As used herein, amorphous has its usual meaning of having no definite form, shapeless, and refers to compositions herein that are liquid based compositions and may have viscosities ranging from 0.001 to $1.6 \times 10^8$ centipoise. As used herein, spreadable means compositions may have a range of viscosities from that of a liquid at room temperature to a composition that is formable into a shape by being manipulated by hand, and that may become less viscous with manipulation or exposure to a different temperature, such as a higher temperature. Compositions of the present invention may comprise amorphous hydrogels, gels, lotions, creams, emulsions and ointments comprising effective amounts of silver ions predominately in the form of a weakly soluble salt, stabilized to retard discoloration by light or irradiation and to control release of the silver ions such that the compositions provide antimicrobial activity when used. The methods of the present invention comprise methods for making the compositions taught herein and methods of use of such compositions for the treatment of burns, wounds, cuts, abrasions or other disruptions of the integrity of the skin or other organs, and uses wherein microbial contamination is an issue, such as in the placement and retention of medical devices in or on living organisms, for example, catheters, trachea tubes, or sutures.

The present invention comprises compositions of amorphous, spreadable materials that are delivery vehicles for sustained release ionic silver antimicrobial activity. Compositions of the present invention comprise spreadable amorphous compositions comprising stabilized antimicrobial silver salt compounds that do not readily discolor when exposed to light, cause little or no staining to skin, garments or cover dressings, and possess sustained release characteristics that increase the period of time that the compositions deliver antimicrobial activity. It is thought the silver ions of the present invention are predominately chemically bound to anionic partners to form a weakly soluble silver salt, and the salt molecules are admixed with various components, including stabilizing agents, may be directly admixed into the amorphous delivery vehicle, or may be form within the amorphous delivery vehicle by addition, in no particular order, of solutions of the silver cation and counter anion to cause the in situ formation of the weakly soluble salt in the amorphous delivery vehicle composition Silver ions that are not stabilized cause materials to turn black or dark colored, and are referred to as readily discolor.

The ionic silver of the present invention is in chemical combination with compounds that form weakly soluble salts of silver. The weakly soluble salt may be any silver salt that is not freely soluble in the delivery formulation. For example, silver chloride is a weakly soluble salt of silver that possesses a solubility product constant of $1.8 \times 10^{-10}$ in aqueous solutions. Other weakly soluble salts of silver may include, but are not limited to, silver saccharin, silver saccharinate silver diazepine complexes, polymeric silver compounds, silver thiocyanate, silver oxide, silver sulfate, silver chloride, silver bromide, silver iodide, silver alkyl carboxylate (C1 to C12), silver aryl sulfonate (C1 to C4 alkyl phenyl), silver carbonate, silver sulfide, silver phosphoranilide, silver phosphate, silver hydroxide, silver hyaluronate, silver benzoate, silver tartarate, silver thiosulfate complex, silver laurate, silver zeolite, silver zirconium phosphate, silver alginate, silver ascorbate, silver folate, silver gluconate, silver salicylate, silver para amino benzoate, silver para amino salicylate, silver acetyl salicylate, silver EDTA, silver laurate, silver zeolite, silver zirconium phosphate, silver alginate, silver ascorbate, silver folate, silver iodate, silver oxalate, silver palmitate, silver perborate, silver stearate, silver succinate, silver thioglycolate, silver hydantoin complex, silver barbiturate, silver allantoinate, silver amine complexes (primary amine, tertiary amine), silver salicylate, silver para amino benzoate, silver para amino salicylate, silver acetyl salicylate, silver EDTA, silver gluconate In one embodiment of the invention, antimicrobial compounds comprise compounds of silver as represented by $M^+X_{(n)}$ wherein, M is silver, n is 1 or more, X is selected from A, B or C where $R_1$ and $R_2$ are —P or —WP; and W is a linker of branched alkyl chain of 1-27 carbon atoms, straight alkyl chain of 1-27 carbon atoms, monoethers containing 2-20 carbon atoms and polyethers containing 2-20 carbon atoms; and P is hydrogen, halogen atoms, haloalkyl, amide, sulfate, phosphate, quarternary ammonium, hydroxyl, hydroxymethyl, phosphonate, amino, carboxyl, carboxymethyl, carbonyl, acetyl, succinimidyl ester, isothiocyanate, isocyanate, iodoacetamide, maleimide, sulfonyl halide, phosphoramidite, alkylimidate, arylimidate, acide halide, substituted hydrazines, substituted hydroxylamines, carbodiimides, cyano, nitro, fluoromethyl, nitrophenyl, sulfonamide, alkenyl or alkynyl; and $R_3$ and $R_4$ are hydrogen, straight alkyl with $C_1$-$C_8$ carbon atoms, optionally terminating in aryl or substituted aryl groups, branched alkyl with $C_1$-$C_8$ carbon atoms, phenyl, substituted phenyl, benzyl, substituted benzyl and fluoromethyl; and A is one of the following:

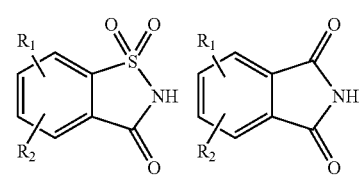

-continued

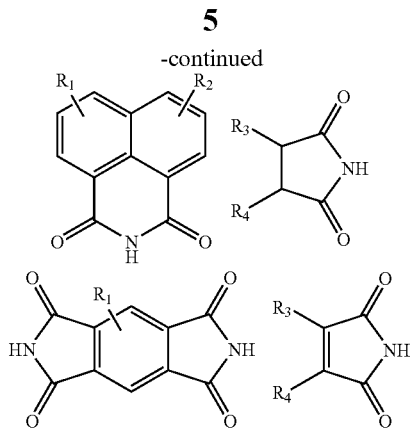

and B is one of the following:

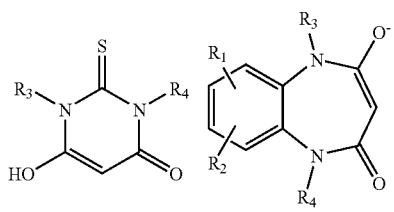

$R_1$ and $R_2$ are —P and —WP as described above, and W is a linker as described above, and $R_3$ and $R_4$ are as described above. C is behenate or bis(2-ethylhexyl)sulfosuccinate.

Another embodiment of the invention comprises complexes of silver comprising $M^+[Y^-]_n$, where M is silver; n is 1 or more; and Y is the following:

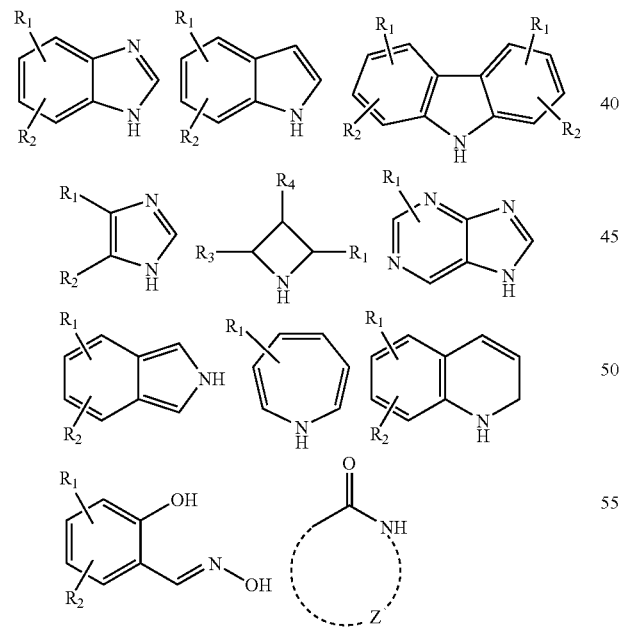

where $R_1$ and $R_2$ are selected from the group consisting of —P and —WP; as described above, and W is a linker as described above. $R_3$ and $R_4$ are described above and Z is C6 or C8 alkyl.

Another embodiment of the present invention comprises the following where $M^+[Y'^-]n$, where M is silver, n is 1 or more, and $Y'^-$ is the following:

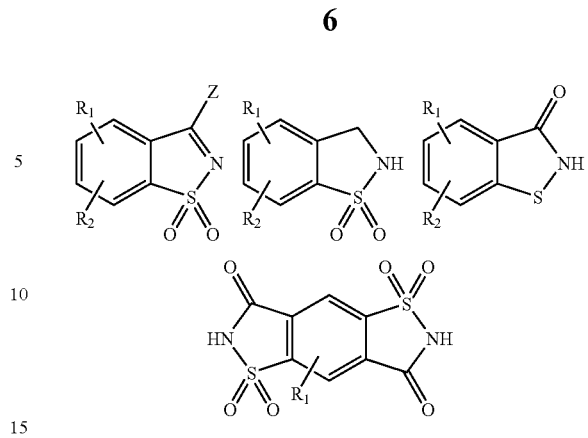

where $R_1$ and $R_2$ are selected from the group consisting of —P and —WP; as described above, and W is a linker as described above. $R_3$ and $R_4$ are described above and Z is amino, alkylamino, chloro, or HNX, wherein X in HNX comprises aryl, hydroxyl, amino, $NHC_6H_5$, or $NHCONH_2$.

Other ligands and anions that form silver salt compounds of the present invention comprise the following shown in Table 1:

TABLE 1

| ID | Name | Structure |
|---|---|---|
| 1.01 | 1,1-Dioxo-1,2-dihydro-1λ⁶-benzo[α]isothiazol-3-one | (structure) |
| 1.02 | Pyrrolo[3,4-f]isoindole-1,3,5,7-tetraone | (structure) |
| 1.03 | Aziridine | (structure) |
| 1.04 | Azetidine | (structure) |
| 1.05 | Isoindole-1,3-dione | (structure) |
| 1.06 | Pyrimidine-2,4,6-trione | (structure) |

TABLE 1-continued

| ID | Name | Structure |
|---|---|---|
| 1.07 | 2-Thioxo-dihydro-pyrimidine-4,6-dione | 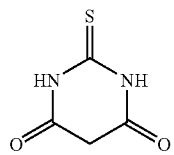 |
| 1.08 | Pyrrole-2,5-dione | 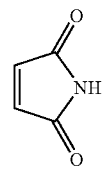 |
| 1.09 | Imidazole-2,4-dione | 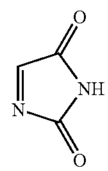 |
| 1.10 | Benzo[de]iso-quinoline-1,3-dione | 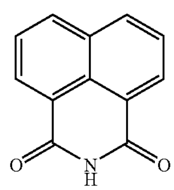 |

The use of weakly soluble salts of silver allow for the slow dissolution of the silver ion in aqueous solutions, such as body fluids, aids in the stability of the silver compound, and promotes the ease of preparation of the compositions taught herein.

Silver salts may discolor when exposed to light. For example, silver chloride discolors to a characteristic purple to pink coloration after exposure to light. Silver saccharinate is less affected by light than silver chloride. Compositions of the present invention comprise stabilized silver which does not discolor in response to light like unstabilized silver. The silver ion is stabilized in the present invention by stabilizing or oxidizing agents. As used herein stabilizing agent may refer to an excess of halide anions such as chloride anions; an excess of one or more organic anions such as saccharinate, or an electron acceptor including, but not limited to, cupric chloride, ferric chloride, zinc chloride, gold, platinum or cesium. Non-limiting examples of oxidizing agents include zinc peroxide or hydrogen peroxide to prevent or delay the reduction of silver ions. The teachings of the present invention include the use of any of the above stabilizing agents or oxidizing agents either individually or in combination. One method of stabilizing the silver in the compositions of the present invention comprises providing anions in an amount that is greater that the amount of silver cations, on a molar basis in the composition, which is also referred to herein as providing an excess of anions. An aspect of a composition of the present invention is the presence of a concentration of anions in excess of the concentration of silver ions for use as a stabilizing agent of the silver. Though not wishing to be bound by any particular theory, it is believed that stabilization of silver may also be achieved by the addition of one or more oxidizing agents that are capable of either competing with silver for the photon activity in light or by scavenging electrons from molecules of reduced silver. Optionally, a composition of the present invention may comprise an oxidizing agent such as compounds comprising copper, iron or zinc compounds or peroxides such as hydrogen peroxide which may function to stabilize the silver. Compositions of the present invention may comprise silver compounds that are weakly soluble silver salts, stabilizing agents that provide excess anions, or oxidizing agents comprising compounds that compete with silver for light photons or energy, or scavenge electrons from molecules of reduced silver, including, but not limited to, copper, iron or zinc compounds, or peroxides, such as hydrogen peroxide.

Compositions comprising silver are known. U.S. Pat. No. 4,604,384 describes limitations of using silver-containing pharmaceutical amorphous gel in the treatment of burns and wounds in the form of black stains to bed linen and some degree of toxic reaction. Dental applications have also used silver as an antibacterial. SilvaSorb Gel, made by AcryMed, Inc., incorporates particles of a hydrophilic polyacrylamide matrix impregnated with silver chloride as taught in U.S. Pat. No. 6,605,751, U.S. patent application Ser. No. 10/441,275 and related international filings, each of which is incorporated by reference herein in its entirety. The particles are admixed in a gel. moisture-containing delivery vehicle formulation. Other matrices incorporating silver are Aquacel Ag (made by Convatec) and SilvaSorb (made by AcryMed, Inc.). Hydrogel sheets are not used in the treatment of patients with large area burns due to manufacturing difficulties, are difficult to apply and secure to large body surface area injuries, and cannot be used in hard to reach areas of the body.

Antibacterial amorphous gels, emulsions or ointments with antibiotics or chlorhexidine derivatives are known. However, these antibiotic-containing materials have limitations. The antibiotic is generally limited to a single site or pathway of action, and prolonged use of antibiotics risks of selecting for bacterial strains that are resistant to the antibiotics. In addition antibiotics are highly selective, resulting in a narrow spectrum antimicrobial activity. In contrast, silver-containing antimicrobial compositions are desired because silver attacks multiple sites on the microbiota. Silver is a true broad spectrum antimicrobial. In addition, its use has never been credibly associated with the selection of resistant strains of organisms.

Though not wishing to be bound by any particular theory, it is currently believed that an advantage of weakly soluble silver salts is the tendency for the silver salt compound to remain in a particulate form at equilibrium with the delivery vehicle formulation. The size of the particulate form of the silver salt compound is thought to range from macroscopic to colloidal. Particle size may be governed by either grinding of a dry silver salt compound or by control of the formation of the silver salt during the mixing processes. One aspect for consideration in making silver-containing compositions is whether the silver salt particles are uniformly distributed throughout the product. One method in which uniformity can be accomplished is to disperse finely grounds salts of silver in the batch during the manufacturing step with stirring or mixing to ensure uniform distribution. An alternative method for forming and dispersing these particles is to sequentially add, in no particular order, the silver cation and the anion(s) either as dry chemical compounds or in solutions, by adding to the carrier vehicle while mixing, to cause uniform distribution of the in situ formed particles of the weakly soluble silver salt. The maintenance of discreetly dispersed particles of the weakly soluble silver salt may be accomplished by causing the formation of cross-links between components of the carrier vehicle. For example, U.S. Pat. No. 6,605,751 teaches a method wherein polyacrylamide polymers are cross-linked after the formation of silver chloride by addition of a silver containing solution and a chloride containing solution. The resulting polymerized article has a uniform distribution of the particles of silver chloride throughout the product. Alternatively the maintenance of uniform dispersion and distribution may be accomplished by viscosity agents in the delivery vehicle formulation that maintain the particles in a state of suspension in the amorphous composition.

The present invention comprises compositions wherein polymers are predominately soluble in the fluid phase of the delivery vehicle. For example, polymers used in the present invention comprise sodium carboxycellulose, carboxymethylcellulose, hydroxyethylcellulose, hydroxypropyl cellulose, or other alkylcellulose derivatives admixed in an aqueous carrier. As the concentrations of these polymers increase in the fluid phase there is a corresponding increase in the viscosity of the delivery vehicle or composition. For example, when these polymers are provided in concentrations greater than approximately 0.5% w/w, they form viscous compositions. While preferring not to be bound by any particular theory, it is proposed that the viscosity of the compositions prevents the settling of the particles of weakly soluble silver salts, and thus aids in the maintenance of a fairly uniform distribution of the silver salts. The compositions may also comprise any amount of cross-linking that will allow the composition to be spread or applied on a surface.

In a similar manner, compositions composed of water-in-oil or oil-in-water emulsions where the weakly soluble salt of silver is either preformed separately and then added to the emulsion or alternatively the salt is caused to form by the sequential addition, in no particular order, of the silver cation and the counter anion during mixing to form the emulsion, or by the addition of the ionic precursors to the water phase prior to its mixing with the oil to make the emulsion. Optionally, the compositions may further comprise stabilizing agents such as an excess of anions alone or in combination with oxidizing agents such as copper, iron or zinc. The resulting composition is a spreadable amorphous antimicrobial composition.

The compositions of the present invention comprise silver salts that are slightly soluble in water, including, but not limited to silver chloride or silver saccharinate, and other silver salts disclosed herein. The compositions may comprise other silver salts that are sparingly soluble in water, such as those having solubility properties differing from those of silver chloride and silver saccharinate. The compositions of the present invention comprise a silver content, as measured by total silver, or concentration of silver salts, of from about 0.005% to about 5.0% wt, from about 0.005% wt to about 2.0% wt, from about 0.05% wt to about 2.0%, from about 0.005% wt to 1.0% wt, and from about 0.05% to 1.0% wt. One embodiment of the compositions has a silver content of less than about 1.0% wt.

Stabilization of the silver to the effects of light may be provided in compositions of the present invention. Stabilization to light may comprise an excess of anions used, and can be provided by an excess amount of salts of chloride and salts of saccharinate, or by saccharin alone. Compositions of the present invention comprise mole ratios of the anionic solutions to silver salt are from 1.1/1, 2/1, and 3/1 to 200/1 and all mole ratios in between. Stability to light may be further provided by use of compositions comprising oxidizing agents that may comprise copper, iron or zinc, or compounds such as peroxides for example hydrogen peroxide, or polyvinyl pyrrolidone-hydrogen peroxide complexes containing up to 20% hydrogen peroxide (Peroxydone K-30 K-90 and XL-10, ISP Corp, Wayne, N.J.). Oxidizing agents such as hydrogen peroxide in concentrations below 5%, based on the total weight of the composition, may be used.

Compositions of the present invention may also comprise active agents such as antibiotics, anti-microbial agents, anti-fungal agents, anti-bacterial agents, anti-viral agents, anti-parasitic agents, mycoplasma treatments, growth factors, proteins, nucleic acids, angiogenic factors, anesthetics, mucopolysaccharides, metals, pharmaceuticals, chemotherapeutic agents, herbicides, growth inhibitors, anti-fungal agents, anti-bacterial agents, anti-viral agents and anti-parasitic agents, wound healing agents, growth promoters, indicators of change in the environment, enzymes, nutrients, vitamins, minerals, carbohydrates, fats, fatty acids, nucleosides, nucleotides, amino acids, sera, antibodies and fragments thereof, lectins, immune stimulants, immune suppressors, coagulation factors, neurochemicals, cellular receptors, antigens, adjuvants or radioactive materials.

Compositions of the present invention comprising stabilized silver may have a pH range of from pH 2 to pH 10, though most applications contemplate physiological pH in the range of about pH 6 to about pH 8.

Optional components of the compositions of the present invention comprise osmagents and osmotically effective compounds. Osmagents are contemplated in the compositions of the present invention. Such compounds are osmotically effective compounds that are soluble in fluids and exhibit an osmotic pressure gradient. Osmotically effective osmagents useful for the present purpose include magnesium sulfate, magnesium chloride, sodium chloride, lithium chloride, potassium sulfate, sodium carbonate, sodium sulfate, lithium sulfate, sodium sulfate, mannitol, urea, sorbitol, inositol, raffinose, sucrose, glucose, glycose, and the like. The osmagent may be present in an excess amount, and it may be in any physical form such a particle, powder, granule and the like. The osmotic pressure in atmospheres (ATM) of the osmagent suitable for the invention will be greater than zero ATM, generally from zero ATM up to 500 ATM, or higher. The amount of active osmagent is blended with the delivery vehicle, and is generally from 0.01% to 40% by weight, or higher. The osmotic pressure of an osmagent can be measured in a commercially available osmometer that measures the vapor pressure difference between pure water and the solution to be analyzed and according to standard thermodynamic principles the vapor pressure ratio is converted into an osmotic pressure difference. An example of an osmometer is Model 320B, Vapor Pressure Osmometer, manufactured by KNAUER, W. Germany and distributed by UTOPIA Instrument Co., Joliet, Ill. 60434.

Compositions of the present invention may comprise delivery vehicle compositions that comprise hydrogels that exhibit fluid absorbing or fluid imbibing properties. A hydrogel comprises hydrophilic, swellable polymers that interact with water and aqueous biological fluids and swell or expand to an equilibrium state. Hydrogels exhibit the ability to swell in aqueous fluids and retain a significant portion of the absorbed or imbibed fluid within the polymer structure. Hydrogels swell or expand to a very high degree, usually exhibiting a 2 fold volume increase, usually a 2 to 50 fold volume increase.

Neutral or ionic hydrogels are contemplated by the present invention. Neutral or ionic hydrogels, and methods for making such gels, are taught by U.S. Pat. No. 4,747,847, which is incorporated by reference herein in its entirety. The compositions of the present invention may comprise such ionic hydrogels and neutral hydrogels as delivery vehicles or delivery compositions, such terms are used interchangeably herein, for the stabilized silver salt amorphous compositions taught herein.

Hydrogel compositions suitable for the present invention comprise hydrogel compositions of plant, animal and synthetic origins. An example of a hydrogel of the present invention comprises a neutral hydrogel. A neutral hydrogel is substantially free of an electrical charge, and is neither acidic or basic, (Hackh's Chemical Dictionary, 4th Ed., p 451, 1969, McGraw Hill Book Co., N.Y.) Representative neutral hydrogels comprise poly(hydroxyalkyl methacrylate) having a molecular weight of 20,000 to 5,000,000; poly(vinylpyrrolidone) having a molecular weight of about 10,000 to 360,000; poly(vinyl alcohol) having a low acetate content and lightly cross-linked with glyoxal, formaldehyde, glutaraldehyde and having a degree of polymerization from 200 to 30,000; poly (ethylene oxide) having a molecular weight from 10,000 to 5,000,000; starch graft copolymers comprising amylose and amylopectin and exhibiting a degree of polymerization from 200 to 10,000,000; cross-linked diester polyglucan having a degree of polymerization from 200 to 10,000,000; cellulose ethers having a degree of polymerization from 200 to 200,000 as exemplified by methylcellulose; hydroxyalkylalkylcellulose including ethylhydroxyethylcellulose, hydroxybutylmethylcellulose; hydroxyethylmethylcellulose and hydroxypropylmethylcellulose; neutral polysaccharides including nonionic compositions such as guar gum, locust bean and tamarind gum, and the like. Hydrogel polymers may include hydrophilic hydrogels prepared from hydrophilic monomers such as monomethacrylates of polethyleneglycols and monoethers, acrylamide and methacrylamide, N-substituted acrylamide and N-substituted methacrylamide, and the like.

An ionic hydrogel is a polymeric hydrogel substituted with at least one chemical group that can dissociate into ions or become electrically charged in the presence of an aqueous type media. (Hackh's Chemical Dictionary, 4th Ed., p 451, 1969, McGraw Hill Book Co., N.Y.) Representative of ionic hydrogels are anionic hydrogels, cationic hydrogels and polyelectrolyte hydrogels. Exemplary ionic hydrogels include carboxymethylcellulose; hydrogels formed of a copolymer of maleic anhydride with styrene, ethylene, propylene, butylene or isobutylene cross-linked with from 0.001 to about 0.5 moles of a polyunsaturated cross-linking agent per mole of maleic anhydride in the copolymer; hydrogels of N-vinyl lactams; acidic carboxy polymers known as carboxypolymethylene and carboxyvinylpolymers, a polymer made of acrylic acid cross-linked with polyallyl sucrose and sold under the trademark (Carbopol®), acidic carboxy polymer having a molecular weight of 200,000 to 6,000,000, including sodium acidic carboxyvinyl hydrogel and potassium acidic carboxyvinyl hydrogel; (Cyanamer®). polyacrylamide; cross-linked indene-maleic anhydride polymers; (Goodrite®) polyacrylic acid polymer having a molecular weight of 60,000 to 500,000; ionic polysaccharides such as anionic carrageenin; anionic agar; anionic gum Arabic; anionic gum ghatti; and the like. Ionic hydrogels including hydrogels prepared from acidic monomers such as acrylic acid; methacrylic acid; crotonic acid; vinyl sulfonate; phosphorylated hydroxyalkylmethacrylates; basic monomers such as aminoalkylmethacrylate, and vinyl pyridine. Polymers which can be used to make such delivery vehicles are known and are taught in the Handbook of Common Polymers, by Scott and Roff, the Chemical Company, Cleveland, Ohio; ACS Symposium Series, No. 31, by Ratner & Hoffman, pp 1 to 36, 1976, the American Chemical Society; and in Recent Advances In Drug Delivery Systems, by Schacht, pp 259-78, 1984, Plenum Press, N.Y.

Compositions of the present invention may comprise viscosities of from about 0.0001 centipoises, to about 2,000,000,000 centipoises, at 25° C., and from about 100 centipoises to about 400,000 centipoises, at 25° C. For example, a neutral hydrogel composition has a viscosity of 150,000 centipoises to 10,000,000 centipoises at temperatures of 40° C. to 45° C. For a composition comprising polyethylene oxide with a molecular weight of 10,000 to 7,000,000, at a 2% solution, the viscosity is generally between 5 to 20,000 centipoises at a room temperature of 23° C.; a polyvinyl pyrrolidone compositions with a molecular weight of between 10,000 to 500,000, for a 10% solution composition, the viscosity is generally between 5 to 5,000 centipoises at 250° C.; for hydroxypropylmethylcellulose composition having a molecular weight of between 1,000 to 200,000, a 2% solution in an aqueous media, the viscosity is from 10 centipoises to 2,000,000 centipoises.

Ionic or anionic hydrogel compositions generally exhibit a viscosity up to 250,000 centipoises, and in the presence of fluid in an animal host, the viscosity may be greater than 250,000 centipoises. The viscosity may be determined by any conventional measurements. The viscosity of a solution can be measured with Wells-Brookfield Viscometer Model LVT, or with a Brookfield Viscometer. Methods and apparatus for measuring viscosity are known in Pharmaceutical Science, by Remington, 14th Ed., pp 359-71, 1970, Mack Publishing Co., Easton, Pa.

Compositions of the present invention may comprise delivery vehicles or delivery compositions known in the art. Delivery vehicles or compositions, include, but are not limited to, components such as propylene glycol, polyethylene glycol of different molecular weights, cellulose ethers such as hydroxymethyl, hydroxyethyl and other higher alkyl derivatives, lactic acid, polyquaternary ammonium polymers known as polyquats, triethanol amine, carbomer polymers of various grades, aminoethyl propanol, di or tetra sodium EDTA, polyvinylpyrrolidone, PVP/Vinyl Acetate copolymer, polyoxyethylene-polyoxypropylene copolymers, sorbitol, poly(n-isopropylacrylamide) polymers, glyceryl polymethacrylates or other acrylates, poly(methacrylic acid), ULTRASIL® copolyols (dimethicone copolyols), siloxane polymers with polyethylene glycols side chains, polyvinyl alcohol, polyethylene oxide polymers, poly(vinyl acetate co-vinyl alcohol).

Other components suitable for silver salt amorphous compositions comprise cellulose ethers such as hydroxyalkyl cellulose (alkyl groups namely methyl, ethyl and propyl), sodium carboxymethyl cellulose, sodium alginate modified with small amounts of calcium or magnesium ions, propylene glycol ester or glyceryl ester of alginic acid, gum karaya, guar gum, gum acacia or gum tragacanth such as those disclosed in U.S. Pat. No. 4,364,929 which is incorporated here in its entirety by reference. Additional examples of components comprise hydratable polyurethane polymers (U.S. Pat. No. 5,175,229), polyalkylene polymers (U.S. Pat. No. 5,593,683), alginates (U.S. Pat. No. 4,393,048 & U.S. Pat. No. 5,693,624), various types of naturally occurring polymers and their derivatives (U.S. Pat. No. 5,804,213), hyaluronic acid and derivatives (U.S. Pat. No. 5,128,326), microbial polysaccharides such as beta-1,3 glucan type polysaccharide (U.S. Pat. No. 5,158,772), acetoacetylated high molecular weight poly vinyl alcohol and hydroxyalkyl cellulose derivatives (U.S. Pat. No. 4,708,821), xanthan gum (U.S. Pat. No. 4,136,177), locust bean gum (U.S. Pat. No. 4,136,178) and beta-cyclodextrin derivatives (U.S. Pat. No. 6,468,989).

Other delivery vehicle compositions comprise block copolymers as disclosed in U.S. Pat. No. 4,130,517 having the general formula xB-[AB]$_n$-yA wherein n is an integer ≥1, x and y are 0 or 1, and y is 1 when n is 1, A is a thermoplastic hydrophobic polymer block, and B is a thermoplastic hydrophilic polymer block. Generally, n is less than 100, or less than 20. Both the A and the B block have a softening temperature (i.e., a glass transition or a crystalline melting point) of at least 35° C. The B block may comprise from about 30 to 97 weight % of the copolymer, from about 50 to 96 weight %, or from about 70 to 95 weight % of the total polymer. The B block may have an average molecular weight of at least 6,000, at least 7,500, or at least 9,000. The average molecular weight of the A block may be at least 2,000, at least 5,000, or at least from about 5,000 to 10,000. The copolymers may have an average molecular weight of at least 10,000, the average molecular weight may be at least 20,000, or the average molecular weight will vary from about 25,000 to 500,000 (number average molecular weight).

The monomers which may be utilized to prepare the hydrophilic block include, but are not limited to, ethylene oxide and alpha-hydroxyethylmethacrylate. The monomers utilized to prepare the hydrophobic polymer block may be selected from the group consisting of styrene, t-butyl styrene, alpha-methyl styrene, vinyl toluene, methyl methacrylate, and polylactones (i.e. poly-epsilon-caprolactone). The hydrophobic block may also be made up of copolymer units so long as the total block is substantially hydrophobic, i.e. water insoluble.

The block copolymers may include ABA copolymers wherein A and B are as previously described. For example, poly-t-butyl styrene-polyethylene oxide-poly-t-butyl styrene, polyvinyl toluene-polyethylene oxide-polyvinyl toluene, polymethylmethacrylate-polyethylene oxide-polymethylmethacrylate, etc. are copolymers for use in the present invention. The block copolymers of this invention may have at least 1 hydrophilic polymer block in the interior of the polymer chain, i.e. the center block of a 3-block copolymer, or one of the two interior blocks of a 4-block copolymer, etc.

Spreadable amorphous antimicrobial devices comprising stabilized silver salts in amorphous delivery vehicles comprising oil-in-water or water-in-oil emulsions are also contemplated in the present invention.

Compositions of the present invention may optionally comprise other components. For example, a colorant may be added to the carrier to create a particular pleasing color or shade. Other components may be added to reduce moisture loss, to improve the firmness, lubricity and/or texture of the compositions.

The present invention also comprises methods of making the stabilized silver salt amorphous compositions disclosed herein. For a silver salt amorphous composition comprising a stabilizing agent, wherein the stabilizing agent is incorporated in the delivery vehicle, the following method may be followed. One method of the present invention comprises a) preparing an amorphous base composition, or delivery vehicle, comprising a stabilizing agent, such as the anion for example, sodium chloride or sodium saccharinate; b) preparing a silver salt mixture by mixing a silver cationic solution and an anionic solution, such as a chloride or saccharinate anionic solution; and c) uniformly mixing the silver salt mixture of b with the delivery vehicle comprising the stabilizing agent. The anionic solution of b may be the same or different from the anion used as the stabilizing agent. For example, if sodium chloride is used as the stabilizing agent, then either sodium chloride or sodium saccharinate, or another anion solution, may be used. Another method of making an amorphous silver salt composition comprising a stabilizing agent, comprises adding in no particular order to the base composition or delivery vehicle, an anionic solution and a cationic silver salt solution, that is soluble, such that the anionic solution concentration is in molar excess of the soluble cationic silver salt solution concentration, mixing to effect the exchange of anion with soluble silver salt to form in-situ in the base composition the weakly soluble silver salt. Another method of making a silver salt amorphous composition comprises a) making the base composition or delivery vehicle b) adding an anionic solution as a stabilizing agent, for example, such as sodium chloride, and an oxidizing agent composition, and mixing to uniformity; c) adding a soluble cationic silver salt solution such as silver nitrate in a concentration less than the anionic solution concentration and mixing uniformly to form the weakly soluble silver salt in situ.

Methods of the present invention comprise methods of making silver salt amorphous compositions comprising surfactants. The silver salt compositions may be made independently from the delivery vehicle and then added to the delivery vehicle to form the final composition, or the silver salt composition may be made in situ from component anionic and silver cationic solutions added, in no particular order, to the delivery vehicle. For example, a surfactant such as Tween 20 (polyoxyethylene sorbitan monolaurate) or similar surfactants can be added to a sodium saccharinate solution to which silver nitrate can then be added to form a suspension of silver saccharinate. The resulting suspension can be added, with mixing, to a delivery vehicle comprising a stabilizing agent to make a silver salt amorphous composition of the present invention. In another example, a surfactant-containing sodium chloride solution can be added to a delivery vehicle composition, with mixing, followed by addition of a soluble silver salt solution to form in situ, a weakly soluble silver salt amorphous composition. Surfactants can be added in amounts up to 5% by weight of the total composition but compositions may comprise one or more surfactants in amounts less than 2% by weight. Surfactants that are GRAS (generally recognized as safe) as defined by FDA regulations are useful in the present invention.

Methods of the present invention comprise treatment of conditions associated with loss of integrity of the skin or other organs, such as, but not limited to, burns, wounds, abrasions, broken skin, cuts or surgical incisions Compositions of the present invention may be used in the treatment of disruptions of the integumentary system, the skin, coverings of organs, mucous membranes, and other coverings of body surfaces, including, but not limited to, wounds, diabetic ulcers, burns, burn wounds and ulcers, skin lesions, and infections of skin and mucous membranes. Compositions of the present invention may be used on living and nonliving surfaces to provide an antimicrobial environment, and may be used for treatment or prevention of infection or pathological conditions in humans, animals and plants.

The compositions of the present inventions can also be used in methods of catheter surface treatment or insertion, or other medical device surface treatment wherein the device is rendered antimicrobial, or topical treatments for skin disorders such as fungal, microbial, or parasitical infections. The present invention can also be used for disinfection means, such as for application to a portion of a mucous membrane, oral, or buccal surfaces. In general, the present invention comprises methods of providing an antimicrobial environment, and methods of treating conditions related to or associated with loss of skin or organ integrity, comprising, applying an antimicrobial silver salt amorphous composition comprising a delivery vehicle admixed with a stabilized silver salt. Methods may comprise providing an antimicrobial environment to a surface by applying an effective amount of a composition taught herein.

The present invention comprising compositions comprising amorphous delivery vehicle compositions and stabilized silver salts, and methods for making and using such compositions. An example of a composition of the present invention comprises a delivery vehicle composition, such as a neutral hydrogel or an emulsion, and a stabilized sodium saccharinate salt. The compositions of the present invention may optionally further comprise one or more of a stabilizing agent, an oxidizing agent, an active agent, and/an osmagent. Delivery vehicles may comprise polymeric compositions comprising an aqueous composition of an alkylcellulose derivative, sodium carboxycellulose, carboxymethylcellulose, hydroxyethylcellulose, or hydroxypropyl cellulose. Delivery vehicles may comprise water-in-oil or oil-in-water emulsions. Delivery vehicles may comprise neutral or ionic hydrogels, or propylene glycol, polyethylene glycol of different molecular weights, cellulose ethers such as hydroxymethyl, hydroxyethyl and other higher alkyl derivatives, lactic acid, polyquaternary ammonium polymers known as polyquats, triethanol amine, carbomer polymers of various grades, aminoethyl propanol, di or tetra sodium EDTA, polyvinylpyrrolidone, PVP/Vinyl Acetate copolymer, polyoxyethylene-polyoxypropylene copolymers, sorbitol, poly(n-isopropylacrylamide) polymers, glyceryl polymethacrylates or other acrylates, poly(methacrylic acid), ULTRASIL® copolyols (dimethicone copolyols), siloxane polymers with polyethylene glycols side chains, polyvinyl alcohol, polyethylene oxide polymers, poly(vinyl acetate co-vinyl alcohol), cellulose ethers, hydroxyalkyl cellulose with alkyl groups methyl, ethyl or propyl, sodium carboxymethyl cellulose, sodium alginate modified with small amounts of calcium or magnesium ions, propylene glycol ester or glyceryl ester of alginic acid, gum karaya, guar gum, gum acacia or gum tragacanth, hydratable polyurethane polymers, polyalkylene polymers, alginates, naturally occurring polymers and derivatives, hyaluronic acid and derivatives, microbial polysaccharides, beta-1,3 glucan type polysaccharide, acetoacetylated high molecular weight poly vinyl alcohol and hydroxyalkyl cellulose derivatives, xanthan gum, locust bean gum, beta-cyciodextrin derivatives or block copolymers having the general formula xB-[AB]n-yA wherein n is an integer ≥1 x and y are 0 or 1, and y is 1 when n is 1, A is a thermoplastic hydrophobic polymer block, and B is a thermoplastic hydrophilic polymer block. Any of the delivery vehicles taught herein may be used to form the amorphous silver salt compositions of the present invention and may optionally comprise one or more of a stabilizing agent, an oxidizing agent, an active agent, and/an osmagent. Where two similar optional agents are used, such as two stabilizing agents, the agents may be the same or different.

The stabilized silver salt compounds of the present invention include the silver salt compounds taught herein, and other antimicrobial silver salt compounds, and are not limited to, silver thiocyanate, silver oxide, silver sulfate, silver alkyl carboxylate (C1 to C12), silver aryl sulfonate (C1 to C4 alkyl phenyl), silver carbonate, silver sulfide, silver phosphoranilide, silver phosphate, silver hydroxide, silver hyaluronate, silver benzoate, silver tartarate, silver thiosulfate complex, silver laurate, silver zeolite, silver zirconium phosphate, silver alginate, silver ascorbate, silver folate, silver gluconate, silver salicylate, silver para amino benzoate, silver para amino salicylate, silver acetyl salicylate, silver EDTA, silver laurate, silver zeolite, silver zirconium phosphate, silver alginate, silver ascorbate, silver folate, silver iodate, silver oxalate, silver palmitate, silver perborate, silver stearate, silver succinate, silver thioglycolate, silver hydantoin complex, silver barbiturate, silver allantoinate, silver amine complexes (primary amine, tertiary amine), silver salicylate, silver para amino benzoate, silver para amino salicylate, silver acetyl salicylate, silver EDTA, or silver gluconate, or wherein the stabilized silver salt comprises $M^+X_{(n)}$ where M is silver, n is 1 or more, X is selected from A, B or C, and where $R_1$ and $R_2$ are —P or —WP; and W is as described herein and P is as described herein; and $R_3$ and $R_4$ are as disclosed herein and A is disclosed as the structures herein, B is as disclosed herein, and C is behenate or bis(2-ethylhexyl)sulfosuccinate. The compositions of the present invention also comprise silver salt compounds wherein the stabilized silver salt comprises $M^+[Y^-]_n$ where M is silver, n is 1 or more; Y is as disclosed herein, where $R_1$ and $R_2$ are —P or —WP; and W is as disclosed herein; and P is as described herein; and $R_3$ and $R_4$ are as disclosed herein; and Z is C6 or C8 alkyl. Silver salt compounds of the present invention also include the stabilized silver salt comprising $M^+[Y^-]_n$ where M is silver, n is 1 or more, and $Y^-$ is as disclosed herein; where $R_1$ and $R_2$ are —P or —WP; and W is disclosed herein; and P is disclosed herein, $R_3$ and $R_4$ are disclosed herein; and Z is amino, alkylamino, chloro, or HNX, wherein X in HNX comprises aryl, hydroxyl, amino, $NHC_6H_5$, or $NHCONH_2$. Other silver salt compounds that are effective in the present invention and are contemplated by the present invention and are taught in copending applications U.S. patent application Ser. No. 11/194,951, PCT/US2005/27260; and PCT/US2005/27261, which are each herein incorporated in their entireties.

Stabilizing agents may comprise an excess of halide ions or anions. Oxidizing agents may comprise copper, zinc or iron compounds, peroxides such as hydrogen peroxide or zinc peroxide, or others taught herein.

Methods of the present invention comprise methods of making antimicrobial amorphous silver salt compositions. Such methods comprise combining delivery vehicle composition components with silver salt composition components to produce an amorphous delivery vehicle comprising a stabilized silver salt. A delivery vehicle may be preformed, thus the components would be combined prior to being combined with silver salt components. Silver salt components comprise the anionic solution and the silver cationic solution. The silver salt solution may be preformed as a silver salt, and not as the component ions, prior to combination with the delivery vehicle, and may be in solid or liquid form. The components of the delivery vehicle or the delivery vehicle composition may be combined with an ionic solution to which a further component of the silver salt composition is added to eventually form the silver salt compound. The methods comprise adding a stabilizing agent to the delivery vehicle and mixing the delivery vehicle with a preformed silver salt solution to form a silver salt amorphous composition.

Methods also comprise wherein the delivery vehicle composition is preformed, further comprising adding in no particular order, an anionic solution and a cationic silver solution to form a silver salt solution in situ in the delivery vehicle, to form a silver salt amorphous composition. Optionally, in the methods taught herein, one or more of the following may be added, an oxidizing agent, a stabilizing agent, an osmagent, and/or an active agent. Where two similar optional agents are used, such as two stabilizing agents, the agents may be the same or different. Methods also comprise wherein the delivery vehicle is an emulsion, and the method comprises combining a water phase component of the delivery vehicle emulsion comprising a silver salt; and adding the water phase to an oil phase to form an antimicrobial amorphous composition.

Methods of the present invention comprise using the compositions taught herein to render surfaces antimicrobial and to prevent infection and microbial growth and attachment or adherence. Methods comprise applying an amorphous silver salt composition comprising an antimicrobially effective amount of a stabilized silver salt to a surface. Methods comprise treating a loss of skin or organ integrity, comprising, applying an amorphous silver salt composition comprising an antimicrobially effective amount of a stabilized silver salt to a site where loss of skin or organ integrity has occurred. Methods comprise treating burns or wounds, comprising, applying an amorphous silver salt composition comprising an antimicrobially effective amount of a stabilized silver salt to a burn or wound.

All terms used herein are considered to be interpreted in their normally acceptable usage by those skilled in the art. Patents and patent applications or references cited herein are all incorporated by reference in their entireties.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

Silver salt antimicrobial amorphous composition of lubricating jelly was prepared as follows. About 8 g of water soluble clear lubricating jelly (Bard Inc., Mansfield, Mass.) was added to a container. A sodium chloride solution (0.05 ml, 0.8M) was added to the jelly followed by silver nitrate solution (0.05 ml, 0.1M) and the contents were vigorously mixed with a spatula. Silver chloride formed and imparted a slight opacity to the jelly composition after about 0.5 h. The silver salt jelly amorphous composition was placed in a clear plastic syringe and left exposed to lab light for 24 h. Negligible discoloration was seen after 24 h. Silver content of the amorphous jelly composition was approximately 0.1% by wt.

Example 2

A silver salt lubricating jelly composition was prepared in a similar manner as Example 1 except the amounts of silver nitrate and sodium chloride were halved. Silver content of the resulting silver salt/jelly amorphous composition was approximately 0.05% by weight. No change in color was observed after 24 h lab light exposure, indicating the silver ion was in a stabilized form.

Example 3

A silver saccharinate composition was prepared by successively adding sodium saccharinate (0.04 ml, 0.125M), hydrogen peroxide (3.3 µl, 30% w/w) and silver nitrate solutions (0.05M, 0.1M). Jelly, water soluble clear lubricating jelly (Bard Inc., Mansfield, Mass.) (8 g) was added to the silver saccharinate composition in a container and the contents were thoroughly mixed. The resulting clear jelly/silver salt amorphous composition was filled into a syringe and exposed to light as in previous examples. Negligible discoloration was seen after 24 h. Silver content was estimated at approximately 0.1% by weight.

Example 4

In a manner similar to Example 3, an antimicrobial jelly/silver salt amorphous composition was prepared except the amounts of sodium saccharinate and silver nitrate solutions were halved. The exposed jelly/silver salt amorphous composition with an estimated silver content approximately 0.05% by weight showed no perceptible change in color after 24 h exposure to incident light.

Example 5

An antimicrobial silver salt jelly amorphous composition was prepared as follows: A silver saccharinate suspension was made by mixing sodium saccharinate (0.025 ml, 0.125M) and silver nitrate (0.025 ml, 0.1M) in a container. KY jelly (4 g) and sodium chloride (0.025 ml, 0.8M) were mixed together and added to the silver saccharinate suspension, and the mixture was then stirred to uniformity. The silver salt containing jelly amorphous composition was clear and had no opacity. After 24 h lab light exposure, no color change was seen. Two weeks after light exposure, the silver salt amorphous composition's color remained unchanged.

Example 6

In this example, a delivery vehicle composition comprising AR grade propylene glycol (25%) w/w); Hydroxyethyl cellulose (2.0% w/w). sodium chloride (0.9% w/w) and distilled water 72.1% w/w) was made. 100 g of this base composition or delivery vehicle was blended with a suspension of silver saccharinate. The suspension of silver saccharinate was prepared by mixing 1 ml of silver nitrate (0.1M) and 1 ml of sodium saccharinate (0.125M).

Example 7

A silver salt amorphous composition was prepared similar to Example 6 except the sodium saccharinate solution (0.125M) also contained Tween 20 surfactant at concentration of approximately 16.5 g/L.

Example 8

A solution of hydroxypropyl cellulose (6.9 g) in de-ionized water (100 ml) was prepared. If needed, the water was warmed. The solution was cooled and 60 g of propylene glycol and 20 ml of sodium chloride (0.4M) were added to the cellulose solution and uniformly mixed. In a separate beaker, 50 ml silver nitrate (0.1M) was slowly poured in a stirred solution of sodium saccharinate (0.125M) containing Tween 20 (approximately 16.5 g/L) to form a white silver saccharinate suspension. To the suspension, 1.5 g glycerin was added and the contents were stirred for few additional minutes. The suspension was then slowly mixed with a prepared hydroxylpropyl cellulose (Spectrum Chemical Co. New Brunswick, N.J.) solution to yield a stabilized silver salt amorphous composition.

Example 9

The amorphous compositions of Examples 1, 2, 4 and 5, prepared above were evaluated for antimicrobial activity in ZOI (Zone of inhibition) assay against *Staphylococcus aureus* bacteria (ATCC 6538). Briefly, small globular amounts of each composition were placed on Mueller Hinton Agar plates freshly inoculated with *Staphylococcus aureus* and incubated at 37° C. for 16 to 24 h. The widths of clear zones around the samples were measured and are shown in Table 1 below. Four amorphous composition exhibited potent antimicrobial activity

TABLE 1

24 h Zone of Inhibition Assay Results against *Staphylococcus aureus*

| Jelly sample | (Clear zone + glob dia/glob dia, mm/mm) |
|---|---|
| Example 1 | 7.5/4.0 |
| Example 2 | 8.0/5.0 |
| Example 4 | 12.0/5.0 |
| Example 5 | 13.0/7.0 |
| Jelly w/o silver (negative control) | 4.5/4.5 |
| Silvasorb dressing (positive control) | 10.0/5.0 |

Example 10

A water soluble clear lubricating jelly (Bard Inc., Mansfield, Mass.) weighing 8 gm was emptied in a container. A sodium chloride solution (0.05 ml, 0.8M) was added with stirring to the jelly and mixed uniformly to disperse the sodium chloride, followed by silver nitrate solution (0.05 ml, 0.1M). A cupric chloride solution (0.025 ml, 0.1M) was added to silver salt/jelly composition and uniformly mixed. The silver salt amorphous composition was filled in a syringe and exposed to light for 24 h. No discoloration was observed.

Example 11

A silver salt amorphous composition was prepared similar to Example 10 except the amount of silver was halved. The corresponding amounts of sodium chloride and cupric chloride were also reduced. The silver salt amorphous composition was filled in a syringe and exposed to light for 24 h. No discoloration was observed.

Example 12

A polymeric delivery vehicle was used to make a silver salt amorphous composition. Two different concentrations were used. One concentration used an acrylamide solution (3 gm of acrylamide in 20 mL water) mixed with 6 gm of 50% w/w solution of AMPS monomer (Lubrizol Inc.), followed by the addition of 1 ml of ammonium persulfate stock (65 mg/ml water) and tetramethyl ethylene diamine (TEMED) (0.08 ml diluted to 1 ml of aqueous solution). The second co-polymer was prepared as before except 3 gm of AMPS monomer solution was used. 2 gm of de-ionized water was added. 0.2 ml of suspension of silver saccharinate was prepared by mixing 0.1 ml each of sodium saccharinate (0.105 M) and silver nitrate (0.1M). The suspension was added to each polymer solution and thoroughly mixed. The resulting polymer amorphous composition was exposed to light for 24 h. Slight color change to beige was observed for the silver salt amorphous composition made from 2:1 ratio of acrylamide to AMPS monomer, but the silver salt amorphous composition having 1:1 ratio turned yellow-brown. A silver salt amorphous composition made with a ratio of 1:2 of acrylamide and AMPS monomer showed only faint color change to beige color in the light exposure test.

Example 13

A radioactive silver salt amorphous composition was prepared as follows. A polymer matrix powder was prepared by dehydrating Acryderm® or Flexigel® dressing and pulverizing the dry dressing. The matrix powder (0.88 gm) was dispersed in glycerol (9.28 gm) to wet it uniformly. To the glycerol/matrix mixture, water (2.54 mL) was added. Next, 6% w/v sodium carboxymethyl cellulose (Hercules Inc.) (20.9 gm) was added and hand mixed. Sodium chloride solution (4.1 ml, 4M) and cupric chloride solution (2.24 ml. 0.1 M) were blended in.

A 10 ml solution of $^{110m}$Ag silver nitrate (0.056 g) was added and hand mixed to form a smooth gel. The radioactive silver salt amorphous composition is useful for animal studies for determining the fate of silver in human body.

Example 14

Silver Salt Emulsion Amorphous Composition

Silver salt amorphous composition emulsion was prepared by hand mixing in a container the oil phase composition and water phase composition.

| Oil Phase Composition | |
|---|---|
| Mineral oil (heavy)- Amresco | 30 g |
| Span 60 - Sigma Aldrich | 6 g |
| Petroleum jelly - Unilever | 5 g |
| PEG 300 - Sigma Aldrich | 5 g |
| Water Phase Composition | |
| Sodium chloride (1M)/Cupric chloride (0.0025M) (1:1 by volume) | 7.5 ml |
| Silver nitrate (0.3 M) | 7.5 ml |
| Tween 20 | 0.05 g |

In preparing the oil phase, under mixing, Span 60 was heated to melting and mixed with mineral oil and petroleum jelly. Separately, the water phase was made by mixing the sodium chloride/cupric chloride salt solution and Tween 20 first and then adding the silver nitrate solution. The resulting water phase and surfactant was mixed with oil phase to form a silver salt emulsion amorphous composition. The emulsion was stable to 4 weeks but then showed signs of separating. It was easily spreadable. In light exposure test the composition showed only minimal to slight discoloration after 72 hours.

Example 15

The silver salt emulsion amorphous composition was prepared in a manner similar to Example 14 but with the oil and water phases with following compositions.

| Oil Phase Composition | |
|---|---|
| Stearic acid | 2.5 g |
| Water Phase Composition | |
| Sodium chloride (1M)/Cupric chloride (0.0025M) (1:1 by volume) | 6.1 ml |
| Silver nitrate (0.3 M) | 6.1 ml |
| Triethanolamine | 0.2 g |
| Glycerol | 1.2 g |

The oil phase was melted and the water phase warmed to 70° C. was then added to the oil phase. The resulting silver salt emulsion amorphous composition was stable, creamy but slightly grainy and not as spreadable as the composition of Example 14. It showed slight discoloration after 72 h of exposure to light.

Example 16

The silver salt emulsion amorphous composition was prepared in a manner similar to Example 14 but with the oil and water phases with following compositions.

| Oil Phase Composition | |
|---|---|
| Stearic acid | 1.25 g |
| Span 60 | 0.25 g |
| Tween 20 | 0.1 g |
| Petroleum jelly | 11.0 g |
| Water Phase Composition | |
| Sodium chloride (1M)/Cupric chloride (0.0025M) (1:1 by volume) | 3.3 ml |
| Silver nitrate (0.3 M) | 3.3 ml |
| Ammonium hydroxide | 0.2 ml |
| PEG 300 | 0.5 g |

The oil phase was melted and the water phase warmed to 70° C. was then added to the oil phase and allowed to cool. The resulting silver salt emulsion amorphous composition was stable and spreadable but had a greasy feel. It showed slight discoloration to grey after 72 h of exposure to light.

Example 17

The silver salt emulsion amorphous composition was prepared in a manner similar to Example 14 but with the oil and water phases with following compositions.

| Oil Phase Composition | |
|---|---|
| Stearic acid | 4.25 g |
| Span 60 | 0.25 g |
| Tween 20 | 0.1 g |
| Petroleum jelly | 8.0 g |
| Water Phase Composition | |
| Sodium chloride (1M)/Cupric chloride (0.0025M) (1:1 by volume) | 3.3 ml |
| Silver nitrate (0.3 M) | 3.3 ml |
| Ammonium hydroxide | 0.2 ml |
| PEG 300 | 0.5 g |

The oil phase was melted and the water phase warmed to 70° C. was then added to the oil phase and allowed to cool. The resulting silver salt emulsion amorphous composition was less greasy, stable and spreadable but had slight grainy feel. It showed slight discoloration to grey after 72 h of exposure to light. When rubbed into skin it exhibited vanishing effect.

Example 18

The silver salt emulsion amorphous composition was prepared in a manner similar to Example 14 but with the oil and water phases with following compositions.

| Oil Phase Composition | |
|---|---|
| Stearic acid | 2.25 g |
| Span 80 | 0.25 g |
| Tween 20 | 0.1 g |
| Petroleum jelly | 9.0 g |
| Mineral Oil (Heavy white) | 1.0 g |
| Water Phase Composition | |
| Sodium chloride (1M)/Cupric chloride (0.0025M) (1:1 by volume) | 3.3 ml |
| Silver nitrate (0.3 M) | 3.3 ml |
| Ammonium hydroxide | 0.2 ml |
| PEG 300 | 0.5 g |

The oil phase was melted and the water phase warmed to 70° C. was then added to the oil phase and allowed to cool. The resulting cream was greasy, stable and spreadable without graininess but slightly stiff feel. It showed slight discoloration to grey after 24 h of exposure to light. When in this example the stearic acid amount was changed to 1.25 g, the resulting cream was not as stiff but retained all other characteristics.

Example 19

The silver salt emulsion amorphous composition was prepared in a manner similar to Example 14 but with the oil and water phases with following compositions.

| Oil Phase Composition | |
|---|---|
| Stearic acid | 1.5 g |
| Span 80 | 0.25 g |
| Tween 20 | 0.1 g |
| Petroleum jelly | 6.75 g |
| Mineral Oil (Heavy white) | 5.0 g |
| Water Phase Composition | |
| Sodium chloride (1M)/Cupric chloride (0.0025M) (1:1 by volume) | 3.3 ml |
| Silver nitrate (0.3 M) | 3.3 ml |
| Ammonium hydroxide | 0.2 ml |
| PEG 300 | 0.5 g |

The oil phase was melted and the water phase warmed to 70° C. was then added to the oil phase and allowed to cool. The resulting silver salt emulsion amorphous composition was somewhat greasy, stable (no separation after 4 weeks) and spreadable. It showed slight discoloration to grey after 24 h of exposure to light.

Example 20

The silver salt emulsion amorphous composition was prepared in a manner similar to Example 14 but with the oil and water phases with following compositions.

| Oil Phase Composition | |
|---|---|
| Stearic acid | 1.25 g |
| Span 80 | 0.25 g |
| Tween 20 | 0.1 g |
| Emulsifying wax | 2.0 g |
| Propylene glycol | 2.0 g |
| Mineral Oil (Heavy white) | 5.0 g |
| Water Phase Composition | |
| Sodium chloride (1M)/Cupric chloride (0.0025M) (1:1 by volume) | 3.3 ml |
| Silver nitrate (0.3 M) | 3.3 ml |
| Ammonium hydroxide | 0.2 ml |
| PEG 300 | 0.5 g |
| Water | 1.75 g |

The oil phase was melted and the water phase warmed to 70° C. was then added to the oil phase and allowed to cool. The resulting silver salt emulsion amorphous composition was grainy in texture and not easily spreadable and stiff.

Example 21

The silver salt emulsion amorphous composition was prepared in a manner similar to Example 14 but with the oil and water phases with following compositions.

| Oil Phase Composition | |
|---|---|
| Stearic acid | 1.25 g |
| Span 80 | 0.25 g |
| Tween 20 | 0.1 g |
| Emulsifying wax | 0.75 g |
| Propylene glycol | 2.0 g |
| Mineral Oil (Heavy white) | 2.0 g |
| Petroleum jelly | 2.0 g |
| Water Phase Composition | |
| Sodium chloride (1M)/Cupric chloride (0.0025M) (1:1 by volume) | 3.3 ml |
| Silver nitrate (0.3 M) | 3.3 ml |
| Ammonium hydroxide | 0.2 ml |
| PEG 300 | 0.5 g |

The resulting silver salt emulsion amorphous composition showed very good consistency and was easily spreadable and stable.

Example 22

The silver salt emulsion amorphous composition was prepared in a manner similar to example A5 but with the oil and water phases with following compositions.

| Oil Phase Composition | |
|---|---|
| Stearic acid | 1.5 g |
| Span 80 | 0.25 g |
| Tween 20 | 0.1 g |
| Mineral Oil (Heavy white) | 5.0 g |
| Petroleum jelly | 4.75 g |
| Water Phase Composition | |
| Sodium chloride (1M)/Cupric chloride (0.0025M) (1:1 by volume) | 4.3 ml |
| Silver nitrate (0.3 M) | 4.3 ml |

The resulting silver salt emulsion amorphous composition had good consistency and but discolored in thick layer after 2 h light exposure to ambient light. On skin after application, it showed no staining.

Example 23

The silver salt emulsion amorphous composition was prepared in a manner similar to Example 14 but with the oil and water phases with following compositions.

| Oil Phase Composition | |
|---|---|
| Stearic acid | 5.25 g |
| Span 80 | 0.44 g |
| Tween 20 | 0.18 g |
| Emulsifying wax | 1.46 g |
| Mineral Oil (Heavy white) | 5.83 g |
| Petroleum jelly | 6.85 g |
| Water Phase Composition | |
| Sodium chloride (1M)/Cupric chloride (0.0025M) (1:1 by volume) | 2.3 ml |
| Silver nitrate (0.3 M) | 2.3 ml |

The resulting silver salt emulsion amorphous composition had very good feel, consistency and stability. It was easily spreadable. It showed little discoloration after 12 h of exposure to ambient light. On skin after application, it showed no staining. The emulsion cream was examined by ZOI assay for broad spectrum antimicrobial activity using 6 clinical isolates strains each of *Staphylococcus aureus* (MRSA), *E coli, Enterococcus faecium, Pseudomonas aeruginosa* and *C. albicans*. Against each type of bacteria, the composition showed potent activity.

Example 24

A cellulose ether derivative, hydroxyethyl cellulose (Spectrum Chemical Co.) was dissolved in deionized water at a concentration of 0.4 gm/12 mL, be adding water to cellulose ether powder in a container and heating to ~80° C. Heating hydrated the powder causing a viscosity increase. The composition was continuously hand mixed as it cooled to room temperature. Glycerol (2 gm) was added and uniformly mixed homogeneity to form a delivery vehicle composition.

In a test tube, a suspension of a weakly soluble silver salt was made using a Tween 20 stock solution (1 mL, 16.7 gm/L), a sodium saccharinate solution (1 mL, 0.125M) and a silver nitrate solution (1 mL, 0.1M) to yield a white suspension. Hydrogen peroxide (0.57 mL, 35% w/w) was added to the suspension.

The test tube contents were added to the delivery vehicle and uniformly blended in to yield an opaque white silver salt composition that could be easily spread. A small amount of composition was placed in a petri-dish and exposed to ambient light. After 24 h exposure, there was a faint color change to a lavender grey shade that was aesthetically acceptable and pleasing. The amount of silver added was ~900 ppm.

Example 25

In a test tube, a suspension of weakly soluble silver salt was made using a Tween 20 stock solution (1 mL, 16.7 gm/L), a sodium chloride solution (1 mL, 0.4 M) and silver nitrate solution (1 mL, 0.1M) successively added to yield a white suspension. The test tube contents were added to a delivery vehicle composition as described in Example 24, and uniformly blended in. A solution of cupric chloride (0.11 mL, 0.1M) and sodium chloride (1 mL, 4M) was then blended into the composition. A small amount of the composition was placed in a petri-dish and exposed to ambient light. After 24 h exposure, there was faint color change to ash grey shade that was still pleasing and aesthetically acceptable.

Example 26

A composition similar to Example 25 except the amount of cupric chloride (0.1M) added was 0.67 mL was made. The resulting composition had a faint bluish hue. A small amount of composition was placed in a petri dish and exposed to ambient light. After 24 h exposure, there was a faint color change to bluish grey shade that was still pleasing. The composition 1 remaining in the dark showed no discoloration after 24 h.

Example 27

A composition similar to Example 26 with addition of (0.28 gm) a powder (Microlattice®, as taught by U.S. Pat. No. 5,196,190), prepared by drying and pulverizing commercially available Acryderm® sheets from AcryMed Inc., Tigard, was made. A small amount of composition was placed in a petri-dish and exposed to ambient light. After 24 h exposure, there was faint color change to a bluish grey shade that was still pleasing. The composition remaining in the dark showed no discoloration after 24 h.

Example 28

A composition similar to Example 24 was made, except that the hydrogen peroxide was omitted. Sodium chloride (1 mL, 4M) solution was added to the silver salt solution prior to mixing with the delivery vehicle. The resulting composition was whitish opaque. A small amount of composition was placed in a petri-dish and exposed to ambient light. After 24 h exposure, there was very faint color change of the composition to lavender grey shade that was unnoticeable. The composition remaining in the dark showed no discoloration after 24 h.

Example 29

A composition similar to Example 26 was made except a mixture of two cellulose ether derivatives—carboxy methyl cellulose sodium salt (0.08 gm) and hydroxylethyl cellulose (0.32 gm) was used to make the delivery vehicle. The CMC-Na salt was purchased from Hercules Inc. (Delaware). The resulting whitish opaque gel had a faint bluish hue. The composition could be easily spread. A small amount of composition was placed in a petri-dish and exposed to ambient light. After 24 h exposure, there was very faint color change to an ash grey shade that was still pleasing. The composition remaining in the dark showed no discoloration after 24 h.

Example 30

Three separate compositions similar Example 26 were made except each used a different cellulose ether derivative—Methyl cellulose, hydroxyl propyl methyl cellulose (Dow Chemical Co.) and hydroxyl propyl cellulose (Spectrum Chemical Co.) in place of hydroxylethyl cellulose. The resulting compositions made from methyl cellulose, hydroxy propyl methyl cellulose (HPMC) and hydroxyl propyl cellulose in appearance were colorless to whitish opaque. The compositions could be easily spread. A small amount of each composition was placed in a petri-dish and exposed to ambient light. After 12 h exposure, there was very faint color change to ash grey shade that was still pleasing. The composition made of HPMC showed the least color change of the three. The compositions remaining in the dark showed no discoloration after 24 h.

Example 31

A composition was prepared using methyl cellulose as follows. A sodium chloride solution (11 mL, 0.4M) and deionized water (1 mL) were warmed to 60° C. and added to cellulose ether powder (0.4 gm) in a container glycerol (2 gm) was added. In a test tube, 1 mL deionized water and a silver nitrate solution (1 mL, 0.1M) were mixed and then poured into container and mixed in. Finally, a cupric chloride solution (0.67 mL, 0.1M) was added and blended in. A portion of the composition was placed in a transparent petri-dish and exposed to ambient light for 24 h. The color of the composition changed to faint ash grey after light exposure. Overall the color change was faint enough yet pleasing. The composition remaining in the dark showed no discoloration after 3 days.

Example 32

A composition was prepared using methyl cellulose as follows. Deionized water (12 mL) were warmed to 60° C. in a microwave oven and added to cellulose ether powder (0.4 gm) in a container and glycerol (2 gm) was added. In a test tube, a sodium chloride solution (1 mL, 0.4M) and a silver nitrate solution (1 mL, 0.1M) were mixed and then re-dissolved by adding enough of an ammonia solution (5.6%) to yield a colorless particle free solution of silver chloride-ammonia complex. The silver complex solution was poured into the container and mixed in. Dilute acetic acid (prepared from 1 part glacial acetic acid and 4 parts water) was added to adjust the pH of the composition to neutral pH (6.5-7.5). A portion of the composition was placed in a transparent petri-dish and exposed to ambient light for 24 h. The color of the glob changed to faint ash grey after light exposure. Overall the color change was faint enough but yet pleasing. The composition remaining in the dark showed no discoloration after 3 days.

What is claimed is:

1. An antimicrobial composition, comprising an amorphous delivery vehicle composition, a stabilized silver salt, wherein the stabilized silver salt comprises silver saccharinate, wherein the stabilized silver salt is stabilized by a molar excess of saccharinate anions to silver ions, wherein the antimicrobial composition is spreadable and resistant to discoloration due to light exposure.

2. The composition of claim 1, further comprising an oxidizing agent.

3. The composition of claim 2, wherein the oxidizing agent comprises copper, zinc or iron compounds, hydrogen peroxide or zinc peroxide.

4. The composition of claim 1, further comprising an active agent.

5. The composition of claim 1, wherein the delivery vehicle comprises a polymeric composition comprising an aqueous composition of an alkylcellulose derivative, sodium carboxycellulose, carboxymethylcellulose, hydroxyethylcellulose, or hydroxypropyl cellulose.

6. The composition of claim 1, wherein the delivery vehicle comprises a water-in-oil or oil-in-water emulsion.

7. The composition of claim 1, wherein the delivery vehicle comprises a hydrogel, a gel, a jelly, a lotion, an ointment, an emulsion, or a cream.

8. The composition of claim 1, wherein the delivery vehicle comprises propylene glycol, polyethylene glycol of different molecular weights, cellulose ethers such as hydroxymethyl, hydroxyethyl and other higher alkyl derivatives, lactic acid, polyquaternary ammonium polymers known as polyquats, triethanol amine, carbomer polymers of various grades, aminoethyl propanol, di or tetra sodium EDTA, polyvinylpyrrolidone, PVP/Vinyl Acetate copolymer, polyoxyethylene-polyoxypropylene copolymers, sorbitol, poly(n-isopropylacrylamide) polymers, glyceryl polymethacrylates or other acrylates, poly(methacrylic acid), dimethicone copolyols, siloxane polymers with polyethylene glycols side chains, polyvinyl alcohol, polyethylene oxide polymers, poly(vinyl acetate co-vinyl alcohol), cellulose ethers, hydroxyalkyl cellulose with alkyl groups methyl, ethyl or propyl, sodium carboxymethyl cellulose, sodium alginate modified with small amounts of calcium or magnesium ions, propylene glycol ester or glyceryl ester of alginic acid, gum karaya, guar gum, gum acacia or gum tragacanth, hydratable polyurethane polymers, polyalkylene polymers, alginates, naturally occurring polymers and derivatives, hyaluronic acid and derivatives, microbial polysaccharides, beta-1,3 glucan polysaccharide, acetoacetylated high molecular weight poly vinyl alcohol and hydroxyalkyl cellulose derivatives, xanthan gum, locust bean gum, beta-cyclodextrin derivatives or block copolymers having the general formula xB-[AB]n-yA wherein n is an integer $\geq 1$, x and y are 0 or 1, and y is 1 when n is 1, A is a thermoplastic hydrophobic polymer block, and B is a thermoplastic hydrophilic polymer block.

9. The composition of claim 1, further comprising an electron acceptor, wherein the electron acceptor comprises cupric chloride, ferric chloride, zinc chloride, gold, platinum, or cesium.

10. A method of making an antimicrobial amorphous silver salt composition, comprising, combining, in no particular order, delivery vehicle composition components with silver salt composition components to produce an amorphous delivery vehicle comprising a stabilized silver salt, wherein the stabilized silver salt comprises silver saccharinate, wherein the stabilized silver salt is stabilized by a molar excess of saccharinate anions to silver ions, and wherein the antimicrobial composition is spreadable and resistant to discoloration due to light exposure.

11. The method of claim 10, wherein the delivery vehicle composition is preformed or prepared first, followed by adding a stabilizing agent to the delivery vehicle composition, and then mixing the delivery vehicle composition with a silver salt solution.

12. The method of claim 10, wherein the delivery vehicle composition is preformed or prepared first, followed by, adding in no particular order, an anionic solution and a cationic silver solution to form a silver salt in situ in the delivery vehicle composition.

13. The method of claim 10, further comprising adding an oxidizing agent, wherein the oxidizing agent comprises copper, zinc or iron compounds, hydrogen peroxide or zinc peroxide.

14. The method of claim 10, further comprising adding an active agent.

15. The method of claim 10, wherein the delivery vehicle is an emulsion, and the method comprises combining a water phase component of the emulsion comprising a silver salt; and adding the water phase to an oil phase to form an antimicrobial amorphous composition.

16. A method of treating or reducing microbial growth or adherence, comprising, applying an amorphous silver salt composition comprising an antimicrobially effective amount of a stabilized silver salt to a surface, wherein the stabilized silver salt comprises silver saccharinate, wherein the stabilized silver salt is stabilized by a molar excess of saccharinate anions to silver ions, and wherein the antimicrobial composition is spreadable and resistant to discoloration due to light exposure.

17. The method of claim 16, wherein the surface is a body site where loss of skin or organ integrity has occurred.

18. The method of claim 16, wherein the surface is a burn or wound.

* * * * *